(12) United States Patent
Bernat et al.

(10) Patent No.: US 6,541,488 B1
(45) Date of Patent: Apr. 1, 2003

(54) COMPOSITIONS FOR TREATING ARTERIAL THROMBOSIS AND A FACTOR XA INHIBITOR

(75) Inventors: André Bernat, Cugnaux (FR); Jean Marc Herbert, Tournefeuille (FR); Maurice Petitou, Paris cedex (FR); Ronald Van Amsterdam, Oss (NL)

(73) Assignees: Sanofi-Synthelabo, Paris (FR); Akzo Nobel, Arnhem (NL)

( * ) Notice: Subject to any disclaimer, the term of this patent is extended or adjusted under 35 U.S.C. 154(b) by 0 days.

(21) Appl. No.: 09/445,555

(22) PCT Filed: Jun. 9, 1998

(86) PCT No.: PCT/FR98/01172
§ 371 (c)(1),
(2), (4) Date: Feb. 11, 2000

(87) PCT Pub. No.: WO98/56365
PCT Pub. Date: Dec. 17, 1998

(30) Foreign Application Priority Data

Jun. 13, 1997 (FR) .............................................. 97 07368

(51) Int. Cl.$^7$ .................... A61K 31/70; A61K 31/445
(52) U.S. Cl. ........................ 514/327; 514/25; 514/317
(58) Field of Search ........................... 514/25, 317, 327

(56) References Cited

U.S. PATENT DOCUMENTS 6,103,705 A    8/2000   Uzan et al. .................... 514/56

FOREIGN PATENT DOCUMENTS

EP      0 138 632      4/1985
EP      0 540 051      5/1993

OTHER PUBLICATIONS

A. Vuillemenot et al, European Heart Journal, vol. 18, p. 622 (1997).
B. Kaiser et al., Blood, vol. 90, No. 10, p. 97B (1997).
Herbert et al., J. Pharmacol. Exp. Ther., vol., 276, No. 3, p, 1030–1038 (1996).
Kunitada et al., Curr. Pharm. Design., vol. 2, No. 5 p. 531–542 (1996).
F. J. Schiele et al., Circulation, vol. 94, No. 8 (1996).
Herbert et al., Cardiovasc. Drug. Rev., vol. 15, No. 1, p. 1–26 (1997).
Cadroy et al., Thrombosis and Haemostasis, vol. 70, No. 4, p. 631–635 (1993).
Zandberg et al., Fibrinolysis, vol. 10, No. supp13, p. 83 (1996).
Van Amsterdam et al., Thromb. Haemost., vol. supp1.6, p. 2384 (1997).
Yamashita et al., Thromb. Res., vol. 85, No. 1, p. 45–51 (1997).
Kaiser, Clin. Appl. Thromb. Hemost., vol. 3, No. 1, p. 16–24 (1997).
Fukuda et al., JPN J. Pharmacol., vol. 71, No. supp. 1, p. 327p (1996).
Vogel et al., Thromb. Haemost., vol. 77, No. 1, p. 183–189 (1997).
Herbert et al., Circ. Res., vol. 79, No. 3, p. 590–600 (1996).
Verstraete et al., Drugs, vol. 49, No. 6, p. 856–884 (1995).
Bernat et al., Fibrinolysis, vol. 10, No. 3, p. 151–157 (1996).
Fitzgerald, Expert. Opin. Ther. Patents, vol. 5, No. 11, p. 1143–1146 (1995).
Herault et al., Blood Coagul. Fibrinolysis, vol. 8, No. 3, p. 206–207 (1997).
Savi et al., Thromb. Haemost., p. 1599, Jun. 1997.
Derwent Patent Abstract No. 198507.

*Primary Examiner*—Theodore J. Criares
*Assistant Examiner*—Jennifer Kim
(74) *Attorney, Agent, or Firm*—Paul E. Dupont; Michael D. Alexander

(57) ABSTRACT

The invention relates to the use of direct or indirect selective inhibitors of factor Xa acting via antithrombin III, alone or in combination with one or more compounds with anti-platelet aggregation activity, for the preparation of medicines intended to prevent and to treat thromboembolic arterial diseases.

Figure 1:
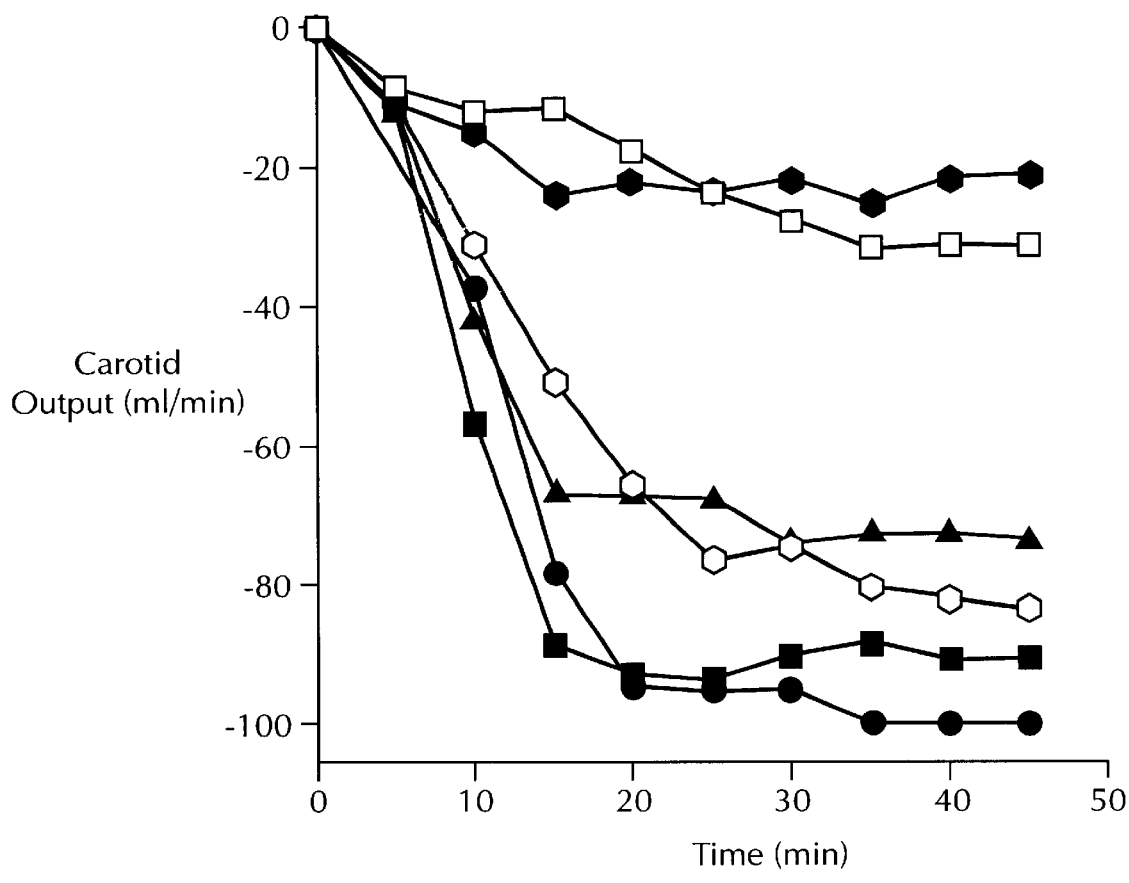
Figure 1:
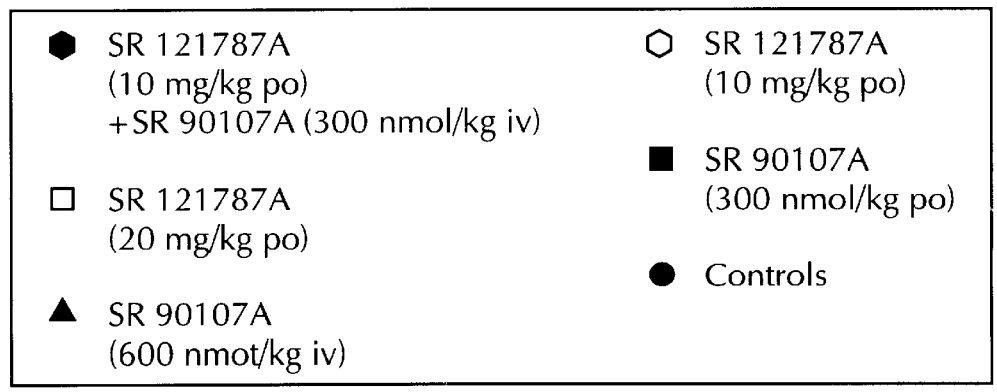

The subject of the invention is also pharmaceutical compositions containing one or more direct or indirect selective inhibitors of factor Xa which act via antithrombin III in combination with one or more compounds with anti-platelet aggregation activity, and optionally one or more pharmaceutically acceptable vehicles.

6 Claims, 1 Drawing Sheet

COMPOSITIONS FOR TREATING ARTERIAL THROMBOSIS AND A FACTOR XA INHIBITOR

The subject of the present invention is the use of direct or indirect selective inhibitors of factor Xa which act via antithrombin III, alone and/or in combination with a compound with anti-platelet aggregation activity, for their activity in arterial thromboembolic diseases.

The pharmaceutical compositions containing the combination of antithrombotic and anti-platelet aggregation active ingredients are also included in the invention. The active ingredients constituting the combination are present in the free state or in the form of one of their pharmaceutically acceptable salts.

During the last decade, a lot of attention has been given to studying the role played by platelets in the development of diseases associated with atherosclerosis (myocardial infarction, angina, cerebral vascular accident, arterial diseases of the lower limbs and the like). Moreover, the well-established role of the blood clotting process in arterial thrombosis has allowed the development of numerous medicines which inhibit various clotting enzymes. The discovery of the essential role of thrombin and factor Xa in the thrombotic process has led to the use of anticoagulants being proposed in the prevention and treatment of arterial thrombosis.

Among the anticoagulants available, heparin is the preferred medicine in the prevention and treatment of thromboembolic diseases.

Heparin catalyses, in particular via anti-thrombin III (AT III), the inhibition of two enzymes which are involved in the blood clotting cascade, namely factor Xa and factor IIa (or thrombin). The relative importance of these two activities in the overall activity of heparin remains unknown. Low-molecular-weight heparin (LMWH) preparations contain chains consisting of 4 to 30 monosaccharides which act like heparin on factor Xa and on thrombin but which have the property of being more selective for factor Xa then for thrombin. In spite of this different biological activity profile, low-molecular-weight heparin has an antithrombotic effect as has been demonstrated in studies on animals and on patients suffering from thromboembolic diseases or at risk of forming a thrombus (Hirsch J. et al., J. Thromb. Hemost., 1987, Leuven, Belgium Leuven University Press, 325–348).

Unlike heparin and the LMWHs, some synthetic oligosaccharides, especially those described in EP 84999, have the property of selectively inhibiting factor Xa via antithrombin III but have no activity on thrombin. These synthetic oligosaccharides which correspond to the antithrombin-binding domain (ABD) of heparin are known and manifest an unthrombotic activity in venous thrombosis. These compounds are described in EP 529715 and EP 621282.

The efficacy of these oligonucleotides in the prevention of arterial thrombosis was hardly probable because of their inability to inhibit thrombin.

Indeed, it has long been known in the literature that thrombin plays a key role in arterial thrombosis and this is again confirmed by recent experiments (L. A. Harker, Blood, 1991, 77. 1006–1012). Thrombin inhibitors therefore constitute an effective means of preventing or combating this type of thrombosis.

It has been observed, by comparing the efficacy of heparin to those of direct thrombin inhibitors (direct inhibitor means an inhibitor which inhibits thrombin without requiring AT III), that they are much more effective than heparin for preventing and treating arterial thrombosis (Arteriosclerosis and thrombosis, 1992, 12, 879–885, J. Am. Coll. Cardiol., 1994, 23, 993–1003). The reason for this lack of efficacy is that the heparin/AT III complex cannot, for reasons to do with steric hindrance, inhibit thrombin in a thrombus rich in platelets as is a platelet thrombus.

The low activity of heparin in contrast to direct inhibitors is therefore linked to its need to use AT III. This explanation is further justified by the recent observation that the direct inhibitors of factor Xa which act without AT III are also effective, in animal models of arterial thrombosis (Circulation, 1991, 84, 1741–1748 Thrombosis Haemost., 1995 74, 640–645).

A compound which, on the one hand, acts via AT III and, on the other hand, does not inhibit thrombin, would therefore be expected to possess no activity in arterial thrombosis.

It has now been found, according to the present invention, quite surprisingly, that a direct or indirect selective inhibitor of factor Xa, alone or in combination with a compound with anti-platelet aggregation activity, can be used for their activity in thromboembolic diseases of arterial origin.

Although it is known to date that the anti-factor Xa agents and the anti-platelet aggregation agents act via two different mechanisms of action, the combination or association of these products for use in arterial thromboembolic diseases has never been studied.

Accordingly, the subject of the present invention is, according to one of its features, the use of one or more direct or indirect selective inhibitors of factor Xa, alone or in combination with one or more compounds with anti-platelet aggregation activity, for the preparation of medicines intended to prevent and to treat thromboembolic diseases of arterial origin.

According to the invention, selective inhibitor of factor Xa is understood to mean a compound capable of selectively inhibiting factor Xa via antithrombin (AT III) but not exhibiting significant activity towards thrombin. Preferably, the inhibitor has no activity towards thrombin.

According to another of its features, the subject of the present invention is also the use of a selective inhibitor of factor Xa which acts via AT III, alone or in combination with a compound with anti-platelet aggregation activity, for the preparation of medicines intended to combat thromboembolic diseases of arterial origin.

Advantageously, the said direct inhibitors of factor Xa are DX-9065a and its analogues. DX-9065a is in particular described in Thromb. Haemost. 1994, 71, 314–319 and in Drugs Fut. 1995, 206, 564–566 and also in EP 540051. Also advantageously, the indirect inhibitors of factor Xa are synthetic oligosaccharides.

Among the direct selective inhibitors of factor Xa, DX-9065a is particularly advantageous, and consists of (2S)-2-[4-[[(3S)-1-acetimidoyl-3-pyrrolidinyl]oxy]phenyl]-3-(7-amidino-2-naphthyl)-propanoic acid hydrochloride pentahydrate in which the acid has the structure (A)

(A)

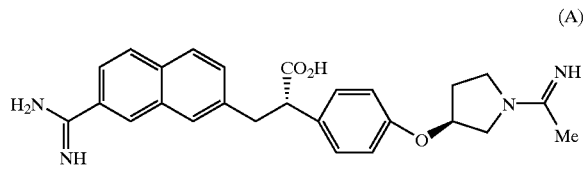

and its pharmaceutically acceptable salts, describes in particular in Thromb. Haemost. 1994, 71, 314–319 and in Drugs Fut. 206, 564–566 and also EP 540051.

Among the indirect selective inhibitors of factor Xa and advantageously, the synthetic oligosaccharides are pentasaccharides, such as those claimed in patents EP 84999 and U.S. Pat. No. 5,378,829.

Particularly advantageous pentasaccharides are in particular:

methyl O-(2-deoxy-2-sulphoamino-6-O-sulfo-α-D-glucopyranosyl)-(1→)-O-(β-D-glucopyranosyluronic acid)-(1→4)-O-(2-deoxy-2-sulphoamino-3,6-di-O-sulpho-α-D-glucopyranosyl-(1→4)-O-(2-O-sulpho-E-L-idopyranosyl-uronic acid)-(1→4)-2-deoxy-2-sulphoamino-6-O-sulpho-α-D-glucopyranoside whose anion has the structure (B)

methyl O-(2,3,4-tri-O-methyl-6-O-sulpho-α-D-glucopyranosyl)-(1→4)-O-(2,3-di-O-methyl-β-D-glucopyranosyluronic acid)-(1→4)-O-(2,3,6-tri-O-sulpho-α-D-glucopyranosyl)-(1→4)-O-(2,3-di-O-methyl-α-L-ido-pyranosyluronic acid)-(1→4)-O-2,3,6-tri-O-sulpho-α-D-glucopyranoside, known under its code name SANORG 34006, whose anion has the structure (D)

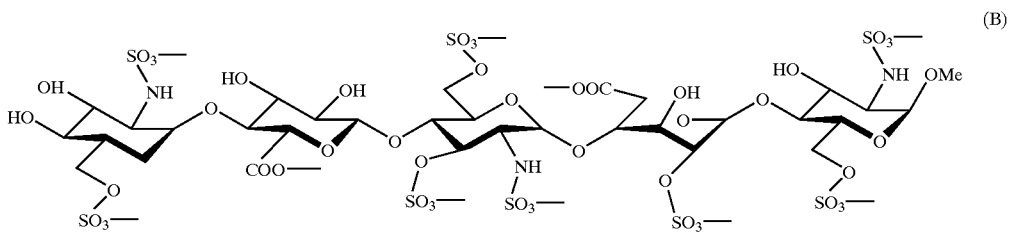
(B)

and its pharmaceutically acceptable salts, in particular its decasodium salt, known under its code name SR 90107/ORG 31540, which is described in Chemical Synthesis to Glycoaminoglycans, Supplement to Nature 1991, 350, 30–33 designated hereinafter "PS";

methyl O-(3,4-di-O-methyl-2,6-di-O-sulpho-α-D-glucopyranosyl)-(1→4)-O-(3-O-methyl-2-O-sulpho-β-D-glucopyranosyluronic acid)-(1→4)-O-(2,3,6-tri-O-sulpho-α-D-glucopyranosyl)-(1→4)-O-(3-O-methyl-2-O-sulpho-α-L-idopyranosyluronic acid)-(1→4)-2,3,6-tri-O-sulpho-α-D-glucopyranoside known under its code name SANORG 32701, whose anion has the structure (C)

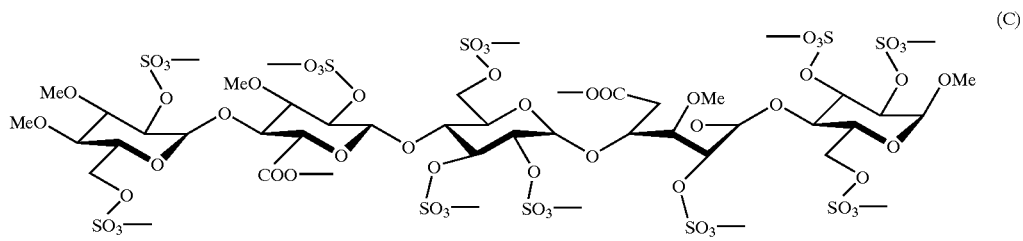
(C)

and its pharmaceutically acceptable salts, in particular its dodecasodium salt, which is described in U.S. Pat. No. 5,378,829;

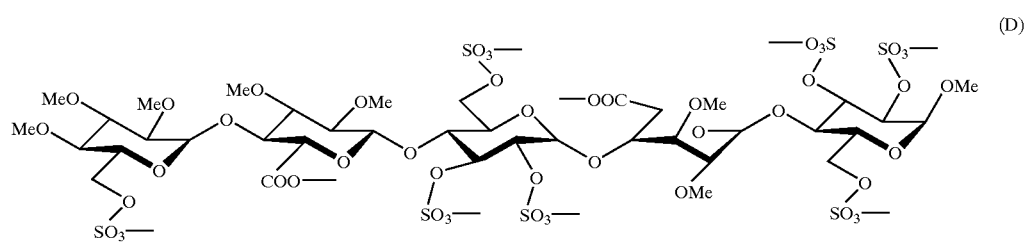
(D)

and its pharmaceutically acceptable salts, in particular its nonasodium salt, which is also described in U.S. Pat. No. 2,378,829.

The anti-platelet aggregation agents which can be used in combination or in association with the oligosaccharides may be of various types, such as for example cyclooxygenase inhibitors such as aspirin, or the anti-platelet aggregation agents described in groups I to L below, such as ADP inhibitors such as ticlopidine and clopidogrel, serotonin inhibitors such as ketanserin, ritanserin, sarpogrelate (MCI-9042), SR 46349 or LY-53857, thromboxane inhibitors such as L 670596, SQ 30741, S-145, AA 2414, CV-6504, HN-11500 and ICI-192,605, thromboxane synthetase inhibitors such as ozagrel (OKY-046), Y-20811, RS-5186, FCE-22178, furegrelate (U-63557A) or mixed thromboxane and thromboxane synthetase inhibitors having the combined effects such as ridogrel (or R-68070) and isbogrel (CV-4151), or inhibitors of the GP IIb-IIIa glyco-protein complex such as c7E3 or abciximab, integrelin, SC 52012, TP 9201, RO 44-9883, RO 43-8857, RO 43-5054, MK 0383 or tirofiban, Dup 728, L 703014, SC 54684, SC 58053, GR 144053, Sibu 104, Bibu 129 or thiazole derivatives such as SR 121787A and SR 121566; FK 633, orbofiban; or compounds increasing the intraplatelet cyclic AMP concentration such as PGEI (alprostadil) and prostacycline (epoprostenol), prostaglandin analogues such as iloprost and beraprost, cicaprost, taprostene, ataprost (OP-41483) and ciprostene or dipyridamole or cilostazol.

The compound of formula (B), preferably in decasodium salt form, is the subject of a preferred use according to, the invention and is also the subject of the preferred antithrombotic for the pharmaceutical compositions of the invention as sole active ingredient or in combination with an anti-platelet aggregation agent.

The anti-platelet aggregation agents are advantageously selected from aspirin or the groups (I) to (L) below;

I—Ticlopidine and Its Analogues of Formula

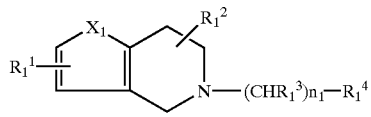

(I)

in which $X_1$ represents oxygen or sulphur; $R_1^4$ represents hydrogen or a phenyl or benzoyl radical optionally substituted with at least one halogen atom or a lower alkyl, lower alkoxy, nitro, amino or sulphonylamino group; $R_1^1$ and $R_1^2$ each represent at least one atom or group selected from hydrogen, a halogen, or a hydroxyl, lower alkyl, lower alkoxy, nitro or amino group; $R_1^3$ represents a hydrogen, a halogen or a hydroxyl, lower alkyl, lower alkoxy, nitro or amino group, and $n_1$ is zero or an integer from 1 to 15, it being possible for the $R_1^3$ symbols to have different meanings in each radical $CHR_1^3$ when $n_1$ is greater than 1, or an addition salt with an acid or a pharmaceutically acceptable quaternary ammonium derivative of this derivative, as described in French patent FR 2,215,948.

II—Clopidogrel and Its Analogues of Formula

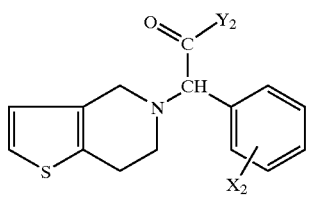

(II)

in which $Y_2$ represents a hydroxyl or a group $OR_2$ in which $R_2$ is a straight or branched alkyl group of 1 to 4 carbon atoms, or $Y_2$ represents a group

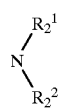

in which $R_2^1$ and $R_2^2$ are each independently of each other hydrogen or a straight or branched alkyl group of 1 to 4 carbon atoms, or $R_2^1$ and $R_2^2$ together form, and with the nitrogen atom to which they are attached, a pyrrolidino, morpholino, piperidino or 4-benzyl-piperazino group; and $X_2$ represents hydrogen, a halogen or an alkyl radical of 1 to 4 carbon atoms; and their addition salts with pharmaceutically acceptable inorganic or organic acids, when $Y_2$ represents the groups $OR_2$ or

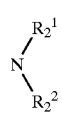

or with inorganic bases when $Y_2$ represents OH, as well as the two enantiomers or their mixture, as described in European patent EP 99802.

III—Ketanserin and Its Analogues of Formula

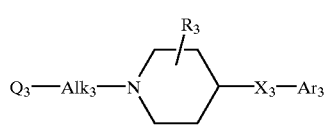

(III)

in which:
Ar$_3$ is an aryl radical;
X$_3$ is a constituent selected from the group consisting of

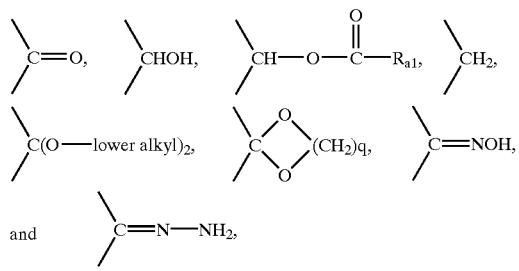

in which the said Ra$_1$ is selected from hydrogen, or a lower alkyl, and q$_1$ is 2 or 3;
R$_3$ is a constituent selected from a hydrogen, a hydroxyl or a lower alkyl;

Alk$_3$ is an alkylene having from 1 to 4 carbon atoms; and

Q$_3$ is a quinazolinyl radical, its 1-, 2-, 3-, 4-position being linked to the end of the alkylene chain, the said quinazolinyl radical carrying at one or at both of its 2- or 4-positions an oxo or thioxo group, in which the benzene ring of the said quinazolinyl radical is optionally substituted with one to three substituents independently selected from the group consisting of a halogen, a lower alkyl, a lower alkyloxy, a trifluoromethyl, a nitro and a cyano, and in which the pyrimidino ring of the said quinazolinyl radical may be partially or completely saturated, it being possible for the said pyrimidino ring to be optionally substituted with one to three substituents independently selected from the group consisting of a lower alkyl, an aryl and an aryl(lower alkyl); in which the said aryl used in the definition of Ar$_3$ and of Q$_3$ is a ring selected from the group consisting of a phenyl, a substituted phenyl, a thienyl and a pyridinyl, in which the said substituted phenyl is substituted with 1 to 3 substituents independently selected from the group consisting of a halogen, a lower alkyl, a lower alkyloxy, a trifluoromethyl or an amino, and its pharmaceutically acceptable addition salts, as described in European patent EP 13612.

IV—Ritanserin or One of Its Analogues of Formula

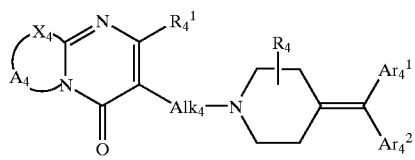

(IV)

in which:

R$_4$ is a hydrogen, a hydroxyl or a lower alkyloxy;

R$^1_4$ is a member of the group consisting of a hydrogen or a lower alkyl;

Alk$_4$ is a lower alkylene radical;

X$_4$ is selected from the group consisting of —S—, —CH$_2$— and —C(R$_4^2$)=C(R$_4^3$)—, the said R$_4^2$ and R$_4^3$ being independently hydrogen or a lower alkyl;

A$_4$ is a bivalent radical having the formula —CH$_2$—CH$_2$—, —CH$_2$—CH$_2$—CH$_2$— or —C(R$^4_4$)=C(R$^5_4$)— in which R$^4_4$ and R$^5_4$ are each independently selected from the group consisting of a hydrogen, a halogen, an amino or a lower alkyl; and Ar$^1_4$ and Ar$^2_4$ are independently selected from the group consisting of pyridinyl, thienyl and phenyl, the said groups being optionally substituted with a halogen, a hydroxyl, a lower alkyloxy and a trifluoromethyl, the isomeric stereochemical forms thereof as well as the pharmaceutically acceptable acid addition salts, as described in European patent EP 110435.

V—Sarpogrelate or One of Its Derivatives of Formula

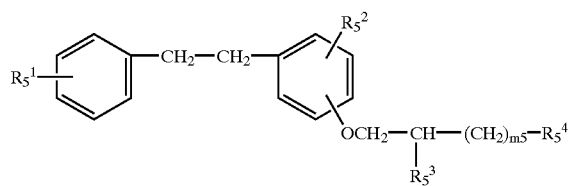

(V)

in which

R$_5^1$ is a hydrogen, a halogen, a (C$_1$–C$_5$)alkoxy or a (C$_2$–C$_6$)dialkylamino;

R$_5^2$ is a hydrogen, a halogen or a (C$_1$–C$_5$)alkoxy;

R$_5^3$ is a hydrogen, a hydroxyl, an —O—(CH$_2$)$_{n5}$—COOH or an —O—CO—(CH$_2$)$_{1_5}$—COOH in which n$_5$ is an integer from 1 to 5 and 1$_5$ is an integer from 1 to 3;

R$_5^4$ is a group

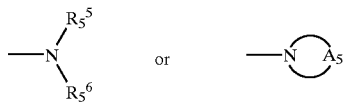

in which

R$^5_5$ and R$^6_5$ are independently a hydrogen or a (C$_1$–C$_8$) alkyl and A$_5$ is a (C$_3$–C$_5$)alkylene or a (C$_3$–C$_5$)alkylene substituted with a carboxyl;

m$_5$ is an integer from 0 to 5; or one of its pharmaceutically acceptable salts, as described in European patent EP 398326.

VI—The Oxime Ethers of Propenone of Transgeometry Relative to the Ethylenic Double Bond of Formula

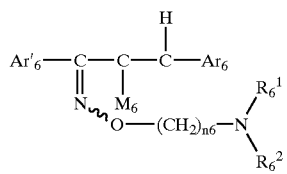

(VI)

in which:

Ar$_6$ and Ar'$_6$ may each independently denote either:

a) a phenyl group which is unsubstituted-or is mono- or polysubstituted with a halogen atom, an alkyl group of 1 to 4 carbon atoms, a nitro group, a hydroxyl group, an alkoxy group of 1 to 4 carbon atoms, an acyloxy group of 1 to 4 carbon atoms, a dimethylamino group, a carboxyalkoxy group in which the alkyl portion contains from 1 to 4 carbon atoms, 9-anthryl or a naphthyl group;

b) a heteroaromatic group selected from the pyridyl, thienyl and furyl groups;

R$_6^1$ and R$_6^2$ each independently denote a hydrogen atom, an alkyl group of 1 to 4 carbon atoms or alternatively R$_6^1$ and R$_6^2$ constitute. with the nitrogen atom to which they are attached a 1-pyrrolidinyl, piperidino, morpholino or 1-piperazinyl group;

M$_6$ represents a hydrogen atom, a chlorine or bromine atom, a straight or branched alkyl group of 1 to 6 carbon atoms;

n$_6$ represents 2 or 3;

as well as their salts with inorganic or organic acids and more particularly the compound known under the code name SR 46349 B, as described in SP 373998.

VII—LY 53857 or One of Its Analogues of Formula (VII)

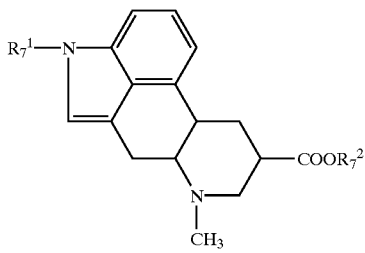

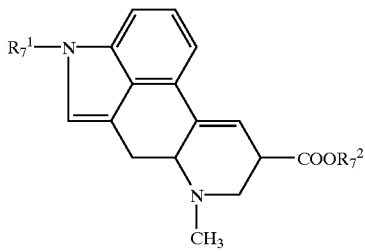

in which $R_7^1$ is a hydrogen, a $(C_1-C_3)$alkyl, an allyl or a benzyl, and $R_7^2$ is a $(C_2-C_8)$monohydroxyalkyl, a $(C_2-C_8)$ dihydroxyalkyl or a monohydroxycycloalkyl having from 5 to 8 carbon atoms and the salts thereof with pharmaceutically acceptable acids, as described in U.S. Pat. No. 3,580,916.

VIII—L 670596 and the Derivatives of Tetrahydrocarbazole-1-alkanoic Acids Consisting of the Compounds of Formula 9-o-chlorobenzyl-6,8-difluoro-1,2,3,4-tetrahydrocarbazol-1-yl-acetic acid;

9-(2,4-dichlorobenzyl)-6,8-difluoro-1,2,3,4-tetrahydrocarbazol-1-yl-acetic acid;

9-p-methylthiobenzyl-6,8-difluoro-1,2,3,4-tetrahydrocarbazol-1-yl-acetic acid;

9-p-methylsulphinylbenzyl-6,8-difluoro-1,2,3,4-tetrahydrocarbazol-1-yl-acetic acid;

9-p-methylsulphonylbenzyl-6,8-difluoro-1,2,3,4-tetrahydrocarbazol-1-yl-acetic acid;

(−)9-p-methylsulphonylbenzyl-6,8-difluoro1,2,3,4-tetrahydrocarbazol-1-yl-acetic acid;

(+) 9-p-methylsulphonylbenzyl-6,8-difluoro-1,2,3,4-tetrahydrocarbazol-1-yl-acetic acid;

9-p-trifluoromethylbenzyl-6,8-difluoro-1,2,3,4-tetrahydrocarbazol-1-yl-acetic acid;

9-p-fluorobenzyl-6,8-difluoro-1,2,3,4-tetrahydrocarbazol-1-yl-acetic acid;

9-m-chlorobenzyl-6,8-difluoro-1,2,3,4-tetrahydrocarbazol-1-yl-acetic acid;

9-p-carbomethoxybenzyl-6,8-difluoro-1,2,3,4-tetrahydrocarbazol-1-yl-acetic acid;

9-p-dimethylcarbamoyl-6,8-difluoro-1,2,3,4-tetrahydrocarbazol-1-yl-acetic acid;

9-p-acetylbenzyl-6,8-difluoro-1,2,3,4-tetrahydrocarbazol-1-yl-acetic acid;

9-p-dimethylaminosulphonylbenzyl-6,8-difluoro-1, 2,3,4-tetrahydrocarbazol-1-yl-acetic acid;

9-p-acetamidobenzyl-6,8-difluoro-1,2,3,4-tetrahydrocarbazol-1-yl-acetic acid;

9-p-methylsulphonamidobenzyl-6,8-difluoro-1,2,3,4-tetrahydrocarbazol-1-yl-acetic acid;

9-p-methylureidobenzyl-6,8-difluoro-1,2,3,4-tetrahydrocarbazol-1-yl-acetic acid and 9-p-methoxybenzyl-6,8-difluoro-1,2,3,4-tetrahydrocarbazol-1-yl-acetic acid;

which are described in EP 300 676.

IX—SQ 30741 as Well as the Compounds of Structure (IX)

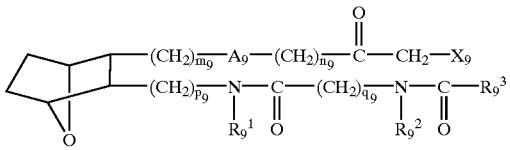

in which $m_9$ is an integer from 0 to 4; $A_9$ is a group —CH=CH— or $CH_2$—$CH_2$—; $n_9$ is an integer from 1 to 5, $X_9$ is a halogen, an alkanoyloxy or a hydroxyl; $p_9$ is 1 to 4; $R_9^1$ is H or a lower alkyl; $q_9$ is an integer from 1 to 12; $R_9^2$ is H or a lower alkyl; and $R_9^3$ is H, a lower alkyl, a lower alkenyl containing from 2 to 12 carbon atoms, an aryl, an arylalkyl, a lower alkoxy, an aryloxy, an amino, an alkylamino or an arylamino; in which the lower alkyl or the alkyl alone or as a constituent of another group contains from 2 to 12 carbon atoms and is unsubstituted or is substituted with a halogen, a $CF_3$, an alkoxy, an aryl, an arylalkyl, a haloaryl, a cycloalkyl, an alkylcycloalkyl, a hydroxyl, an alkylamino, an alkanoylamino, an arylcarbonyl amino, a nitro, a cyano, a mercapto or an alkylthio; the aryl alone or as a constituent of another group contains from 6 to 10 carbon atoms on the cyclic portion and is unsubstituted or is substituted with one or two lower alkyls, 1 or 2 halogens, 1 or 2 hydroxyl groups, 1 or 2 lower alkoxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 mercapto groups and/or 1 or 2 alkylthio groups; and the cycloalkyl alone or as a constituent of another group contains from 3 to 12 carbon atoms, is unsubstituted or is substituted with 1 or 2 halogens, 1 or 2 lower alkyl groups, 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 mercapto groups and/or 1 or 2 alkylthio groups; $(CH_2)_{m9}$, $(CH_2)_{n9}$ and $(CH_2)_{p9}$ may be substituted with 1 or 2 lower alkyl and/or 1 or 2 halogen substituents; and $(CH_2)_{q9}$ may be substituted with one or more halogen, hydroxyl, alkoxy, amino, alkylamino, arylamino, carbamoyl, thiocarbamoyl, mercapto, alkylthio, arylthio, cyano or nitro groups; as well as all its stereoisomers, as described in U.S. Pat. No. 4,638,012.

X—S-145 and the Compounds of Formula (X)

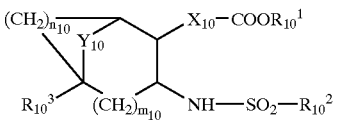

in which:

$R_{10}^1$ is a hydrogen or a lower alkyl;

$R_{10}^2$ is a substituted or unsubstituted aryl, an aralkyl or a heterocycle;

$R_{10}^3$ is a hydrogen or a methyl;

$X_{10}$ is an alkylene or an alkenylene which may be substituted with one or more fluorine atoms and whose chain may be interrupted by an oxygen, a sulphur and/or a phenylene;

$Y_{10}$ is a straight or branched alkylene or an alkenylene, an oxygen or a sulphur;

$m_{10}$ is 0 or 1:

$n_{10}$ is 0, 1 or 2, which are described in EP 226 346.

XI—AA 2414 and the Compounds of Formula

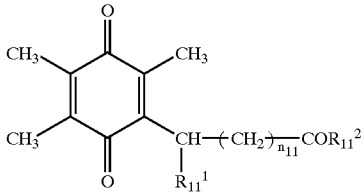

(XI)

in which:

$R_{11}^1$ is optionally a substituted phenyl group, $R_{11}^2$ is optionally a substituted amino group and $n_{11}$ is an integer from 3 to 10 or a hydroquinone derivative thereof, as described in EP 232 089 A2.

XII—CV 6504 and the Compounds of Formula

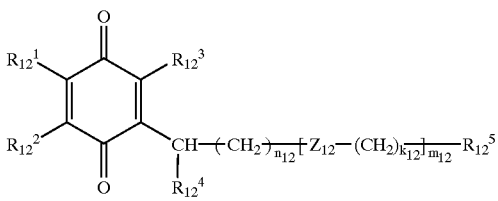

(XII)

in which:

$R_{12}^1$ and $R_{12}^2$, which are identical or different, represent a hydrogen atom, a methyl or hydroxyl group, or alternatively $R_{12}^1$ and $R_{12}^2$ are linked so as to form —CH=CH—CH=CH—;

$R_{12}^3$ is a hydrogen atom or a methyl group;

$R_{12}^4$ is a heterocyclic group containing a nitrogen atom which may be substituted;

$R_{12}^5$ is a hydrogen atom, a methyl or hydroxymethyl group which may be substituted, or a carboxyl group which may be esterified, or in the form of an amide;

$Z_{12}$ is

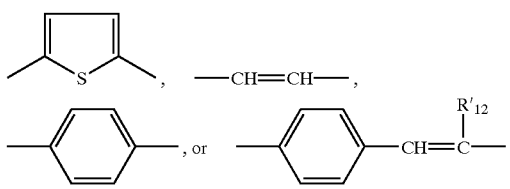

in which $R'_{12}$ is a hydrogen atom or a methyl group;

$n_{12}$ is an integer from 0 to 12, $m_{12}$ is an integer from 0 to 3, and $k_{12}$ is an integer from 0 to 7, with the proviso that when $m_{12}$ is 2 or 3, $Z_{12}$ and $k_{22}$ are capable of varying appropriately in the repeated unit described in [ ] and the hydroquinone derivatives of those described in EP 234729.

XII—HN 11500, Linotroban As Well as the 2-thienyloxyacetic Acid Derivatives of Formula

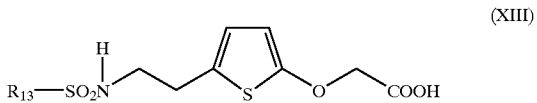

(XIII)

in which $R_{13}$ is a phenyl or thienyl group which is substituted, where appropriate, once or several times with a halogen atom, a trifluoromethyl group or an alkyl group of 1 to 4 carbon atoms, as well as their pharmaceutically acceptable salts, as described in EP 284 892.

XIV—CI 192605 or a 2,4-diphenyl-1,3-dioxane Derivative of Formula

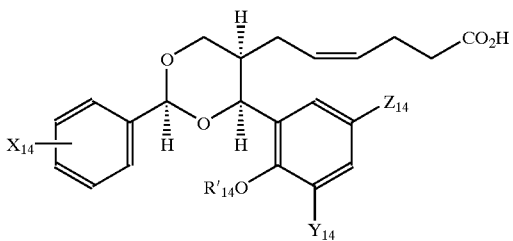

(XIV)

in which:

$X_{14}$ is F, Cl, Br, CF3, CN, OMe or $NO_2$;

$Y_{14}$ or $Z_{14}$ is independently hydrogen or F and the other is hydrogen; and $R'_{14}$ is a $(C_1–C_6)$alkyl;

the groups at the 2-, 4- and 5-positions of the dioxane ring having a cis stereochemistry, as well as their pharmaceutically acceptable salts, as described in EP 201354.

XV—OKY 046 or Ozagrel and Its Analogues of Formula

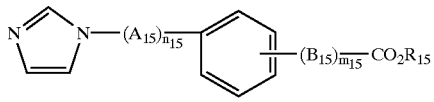

(XV)

in which:

$R_{15}$ is a hydrogen atom or a $(C_{11}–C_6)$alkyl group;

$A_{15}$ and $B_{15}$, which are identical or different, represent a bond, a straight or branched $(C_1–C_8)$alkylene or a $(C_2–C_8)$alkenylene;

$n_{15}$ and $m_{15}$, which are identical or different, are 0 or 1, whereas Air and Bis consist of 2, 3 or 4 carbon atoms, as well as its pharmaceutically acceptable salts, as described in DE 2,923,815.

XVI—Y 20811 and the Imidazole Derivatives of Formula

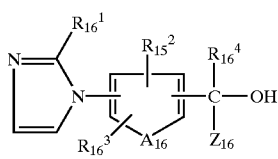

(XVI)

in which:

each of the groups $R_{16}^1$ and $R_{16}^4$ is a hydrogen atom or a $(C_1–C_4)$alkyl group;

each of the groups $R_{16}^2$ and $R_{16}^3$ is a hydrogen atom, a halogen atom, a hydroxyl group, a ($C_1$–$C_4$)alkyl group, a ($C_1$–$C_4$)alkoxy group, a benzyloxy group, a phenethyloxy group, a nitro group or an amino group;

$A_{16}$ is an —O—, —S—, —CH═CH— or —CH═N— group;

$Z_{16}$ is a phenyl group, a naphthyl group, a thienyl group, a pyridyl group or a furyl group, in which definition these (heterocyclic) aromatic rings comprise 1 to 3 sub3tituents, each substituent being independently selected from a halogen atom, a ($C_1$–$C_4$)alkyl group, a ($C_3$–$C_6$)cycloalkyl group, a ($C_1$–$C_4$)alkoxy group, a hydroxyl group, a carboxyl group, a ($C_1$–$C_4$) alkoxycarbonyl group, a carboxy ($C_1$–$C_4$ alkoxy) group, a ($C_1$–$C_4$)dialkylamino($C_1$–$C_4$ alkoxy) group and a nitro group, or an addition salt of this derivative with a pharmaceutically acceptable acid, as described in EP 110996.

XVII—RS 5186 and the Compounds of Formula

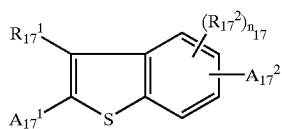

(XVII)

in which:

$R_{17}^1$ and $R_{17}^2$ are identical or different and each represent a hydrogen atom, a ($C_1$–$C_4$) alkyl group, a carbocyclic ($C_6$–$C_{10}$)aryl group or a substituted carbocyclic cyclic ($C_6$–$C_{10}$)aryl group having at least one of the substituents (a) below;

$n_{17}$ is 1 or 2;

one of $A_{17}^1$ or $A_{17}^2$ represents a group of formula $Z_{17}$–$Y_{17}$ in which $Y_{17}$ represents an imidazolyl or pyridyl group and $Z_{17}$ represents a methylene, ethylene, trimethylene or vinylene group or a methylene, ethylene, trimethylene or vinylene group having at least one of the substituents (b) below;

the other, which is either $A_{17}^1$ or $A_{17}^2$ represents a group of formula —$W_{17}$—COOH, in which $W_{17}$ represents a bond, a methylene group, a ═CH— group, an ethylene group, a vinylene group, the said group being optionally substituted with at least one of the substituents (c) below, with the proviso that $W_{17}$ represents only the said ═CH— group when $A_{17}^1$ represents the said group —$Z_{17}$–$Y_{17}$;

$A_{17}^2$ is at the 5- or 6-position of the bicyclic system;

each dotted line represents a carbon-carbon single or double bond between the 4- and 5- or 6- and 7-positions, it being understood that when $A_{17}^2$ is at the 5-position, the bond between the 6- and 7-positions is a single bond and that when $A_{17}^2$ is at the 6-position, the bond between the 4- and 5-positions is a single bond;

the substituents (a) being ($C_1$–$C_4$)alkyl groups, ($C_1$–$C_4$) alkoxy groups, aliphatic carboxylic ($C_2$–$C_6$)acyloxy groups, aromatic carboxylic acyloxy groups, aliphatic carboxylic ($C_2$–$C_5$)acylamino groups, aromatic carboxylic acylamino groups, trifluoromethyl groups, halogen atoms, nitro groups, cyano groups, amino groups, ($C_1$–$C_4$)alkylamino groups, dialkylamino groups in which each alkyl portion is a ($C_1$–$C_4$), carboxyl groups and esters and amides of the said carboxyl groups, the acyl portions of the said aromatic acyloxy groups and of the aromatic acylamino groups being carbocyclic ($C_6$–$C_{10}$)aryl groups which are unsubstituted or which are at least substituted with a ($C_1$–$C_4$)alkyl, a ($C_1$–$C_4$)alkoxy or a halogen substituent;

the substituents (b) being ($C_1$–$C_4$)alkyl groups, ($C_3$–$C_6$) cycloalkyl groups, ($C_6$–$C_{10}$)aryl groups, ($C_6$–$C_{10}$)aryl groups substituted with at least one substituent (a) and the heterocyclic groups having from 5 to 10 atoms in the ring, in which 1 to 3 of the said atoms are nitrogen and/or oxygen and/or sulphur heteroatoms, the said heterocyclic groups being unsubstituted or having at least one substituent selected from (a), (c) or oxygen atoms; and the substituents (c) being ($C_1$–$C_4$)alkyl groups, ($C_6$–$C_{10}$) aryl groups and substituted ($C_6$–$C_{10}$)aryl groups having at least one substituent (a) and its pharmaceutically acceptable salts, its amides and its esters, as described in EP 240 107.

XVIII—FCE 22 17B and the Compound of Formula

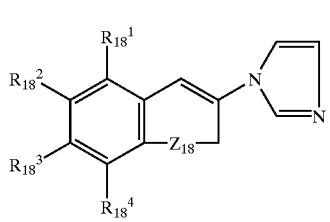

(XVIII)

in which:

the symbol ══ represents a single or double bond;

$Z_{18}$ represents a single bond or is a —$CH_2$— group;

$R_{18}^1$, $R_{18}^2$, $R_{18}^3$, and $R_{18}^4$ are identical or different and represent (a) a hydrogen, a hydroxyl, a halogen, a ($C_1$–$C_4$)alkyl, a ($C_1$–$C_4$)alkoxy, a ($C_2$–$C_4$)acyl or hydroxymethyl, a ($C_1$–$C_4$)alkanoyl, a $CONH_2$, or a $COOR'_{18}$ in which $R'_{18}$ represents a hydrogen or a ($C_1$–$C_4$)alkyl; or (b) a residue from $R_{18}^1 R_{18}^2$, $R_{18}^3$ and $R_{18}^4$ represents —CH═CH—$COOR'_{18}$ or an —O—$C(R'_{18}R''_{18})$ $COOR'_{18}$ or a ($C_1$–$C_4$)alkyl, the other residues having the meaning defined above in (a), as well as their pharmaceutically acceptable salts, as described in DE 33 24 069.

XIX—Furegrelate and its analogues of formula:

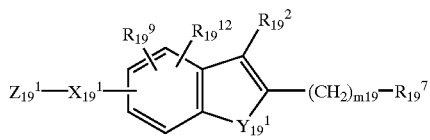

(XIX)

in which:

$Z_{19}^1$ is 4-pyridinyl, 3-pyridinyl, 4-methyl-3-pyridinyl, 4-methoxy-3-pyridinyl, 4-dimethylamino-3-pyridinyl, 4-amino-3-pyridinyl, 4-dimethylamino-3-pyridinyl, 4-amino-3-pyridinyl, 2-, 4-, 5- or 6-chloro-3-pyridinyl, an imidazolyl or a (($C_1$–$C_3$)alkyl)imidazolyl;

$X_{19}^1$ is —$(CH_2)n_{19}$—, —O—, —S—, —SO—, —$SO_2$— —$CH_2$—O—, —O—$CH_2$—, —$CH_2$—NR193-, —$NR_{19}^3$—$CH_2$—, —CHOH— or —CO— in which $n_{19}$ is an integer from 0 to 4 and $R_{19}^3$ is a hydrogen, a methyl, with the proviso that $Z_{19}^1$ is an optionally substituted pyridinyl as defined above when $X_{19}^1$ is not —$(CH_2)_{n19}$—, —CHOH— or —O—$CH_2$—; $Y^1{}_{19}$ is an oxygen or sulphur atom, provided that $X^1{}_{19}$ is not —SO— or —$SO_2$— when $Y^1{}_{19}$ is —S—;

$R_{19}^2$ is a hydrogen, a $(C_1-C_3)$alkyl, a phenyl, or —$COOR_{19}^1$; in which $R_{19}^1$ is hydrogen, a pharmaceutically acceptable cation, a $(C_1-C_{12})$alkyl, a $(C_1-C_3)$ cycloalkyl, a $(C_7-C_{12})$aralkyl, a phenyl optionally substituted with up to 3 substituents independently selected from chlorine, a $(C_1-C_3)$alkyl, or a phenyl para-substituted with an —NHCO—$R_{19}^{25}$, —O—CO—$R_{19}^{26}$, —CO—$R_{19}^{24}$, O—CO—(p—Ph)—, $R_{19}^{27}$ or —CH—N—NH—CO—$NH_2$ in which $R_{19}^{24}$ is a phenyl or an acetamidophenyl, $R_{19}^{25}$ is methyl, phenyl, acetamidophenyl, benzamidophenyl or an amino, $R_{19}^{26}$ is a methyl, phenyl, an amino or a methoxy, $R_{19}^{27}$ is a hydrogen or an acetamido, and p—Ph is a 1,4-phenylene;

$R_{19}^7$ is a hydrogen, —$CH_2OH$—; —$COOR^1{}_{19}$, in which a $R_{19}^1$ is as defined above, —CN or —$CH_2N(R_{19}^4)_2$, CO—$N(R_{19}^4)_2$ or —CO—$R_{19}^4$ in which $R_{19}^4$ is a hydrogen, a $(C_1-C_4)$alkyl, or a phenyl;

either $R_{19}^9$ and $R_{19}^{12}$ are independently selected from a hydrogen, hydroxyl, $(C_1-C_4)$alkyl, fluorine, chlorine, bromine and methoxy, or $R_{19}^9$ and $R_{19}^{12}$ are bonded to adjacent carbon atoms and together represent —O—$CH_2$—O—;

...... represents a single bond (in this case, the compound may be an enantiomer or a racemate) or a double bond;

$m_{19}$ is an integer from 0 to 4;

or one of its pharmaceutically acceptable acid addition salts, as described in EP 069 521.

XX—Ridogrel or one of its analogues of formula:

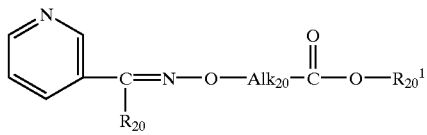

(XX)

in which:
$R_{20}$ is a hydrogen, a $(C_1-C_{10})$alkyl, a trifluoromethyl, an $Ar_{20}$ radical or a radical $Ar_{20}$—$(C_1-C_{10})$alkyl; in which $Ar_{20}$ is a phenyl, a naphthyl, a pyridinyl, a pyrimidinyl, a furanyl or a thienyl, the said phenyl and naphthyl being optionally substituted with up to 3 substituents independently selected from $(C_1-C_6)$alkyl, $(C_1-C_6)$ alkoxy, a mono- and di$((C_1-C_6)$alkyloxy)methyl, an amino, a $(C_1-C_5)$alkylcarbonylamino, a carboxyl, a formyl, a halogen, a hydroxyl, a nitro and a trifluoromethyl;

$R_{20}^1$ is a hydrogen or a $(C_1-C_6)$alkyl; and $Alk_{20}$ is a $(C_2-C_{10})$alkylene radical; with the proviso that the radical $C_5H_4N$—$C(R_{20})$=N—C— and the radical —$COOR_{20}^1$ are not bonded to the same carbon atom, it being possible for these compounds to be in the form of an N-oxide, of an addition product with a pharmaceutically acceptable acid, of a metal salt or of an ammonium salt, or a stereochemically isomeric form of these .compounds, as described in EP 221601.

XXI—Isbogrel and its analogues of formula:

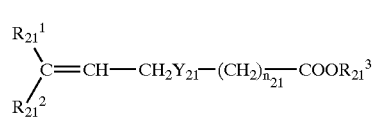

(XXI)

in which:
$R_{21}^1$ is a pyridyl group, $R_{21}^2$ is a phenyl group, a thienyl group, a furyl group, a naphthyl group, a benzothienyl group or a pyridyl group which may be optionally substituted with a lower alkoxy group, a lower alkyl group, a halogen atom, a trifluoromethyl group, a lower alkenyl group or a methylenedioxy group, $R_{21}^3$ is a hydrogen atom or a lower alkyl group, and $n_{21}$ is an integer from 0 to 6, as described in EP 098 690.

XXII—Abciximab, a class $IgG_1$ monoclonal antibody manufactured according to WO/06133.

XXXII—Integrelin and its analogues containing at least 5 contiguous amino acids of an oligopeptide selected from:
(a)
  Gly-Ser-Pro-Arg-Cys-Asp-Leu-Lys-Glu-Asn-Leu-Leu-Lys-Asp-Asn-Cys-Ala-Pro-$Z_{23}$;
(b)
  Ala-Arg-Val-Leu-Glu-Asp-Arg-Pro-Leu-Ser-Asp-Lys-Gly-Ser-Gly-Asp-Ser-Ser-Gln-Val-$Z_{23}$;
(c)
  Asp-Gln-Val-Thr-Arg-Phy-Asn-Glu-Glu-Val-Lys-Lys-Gln-Ser-Val-Ser-Arg-Asn-Arg-Asp-$Z_{23}$;
(d)
  Glu-Glu-Val-Lys-Lys-Gln-Ser-Val-Ser-Arg-Asn-Arg-Asp-Ala-Pro-Glu-Gly-Gly-Phe-Asp-$Z_{23}$ et
(e)
  Asn-Glu-Glu-Val-Lys-Lys-Gln-Ser-Val-Ser-Arg-Asn-Arg-Asp-Ala-Pro-Glu-Gly-Gly-Phe-Asp-Ala-lle-Met-Gln-Ala-$Z_{23}$;
(f)
  Ser-Val-Ser-Arg-Asn-Arg-Asp-Ala-Pro-Glu-Gly-Gly-Phe-Asp-Ala-lle-Met-Gln-Ala-$Z_{23}$; or
(g)
  Ser-Val-Ser-Arg-Asn-Arg-Asp-Ala-Pro-Glu-Gly-Gly-$Z_{23}$; in which $Z_{23}$, if present, is OH and the oligopeptide has less than 50 combined native amino acids described in WO 90/00178.

XXIV—SC 52012 and its analogues of formula:

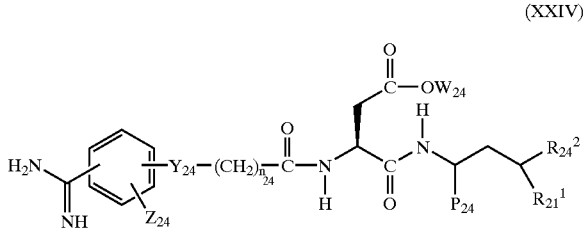

(XXIV)

in which:
$R_{24}^1$ and $R_{24}^2$ are each independently selected from hydrogen; a phenyl; a substituted phenyl in which each substituent may be selected from a group consisting of a $(C_1-C_6)$alkyl, a halogen, a $(C_1-C_6)$alkoxy, a trifluoromethyl, a hydroxyl and a carboxyl; a $(C_1-C_6)$ alkyl; a heterocycle consisting of a 5- or 6-membered ring comprising a heteroatom selected from: nitrogen, oxygen and sulphur, fused with a benzene ring;

$P_{24}$ is hydrogen, a carboxyl or a $(C_1-C_6)$alkoxycarbonyl, $W_{24}$ is hydrogen or a $(C_1-C_6)$alkyl;

$Y_{24}$ is a methylene, a $(C_2-C_4)$alkenyl, a $(C_2-C_4)$alkynyl or a carbonyl;

$Z_{24}$ is a halogen, a $(C_1-C_6)$alkoxy, a $(C_1-C_6)$alkyl or a hydrogen;

$n_{24}$ is an integer from 1 to 6;

with the proviso that when $P_{24}$, $W_{24}$ and $Z_{24}$ each represent hydrogen, $Y_{24}$ is a methylene at the meta position of the aminoiminomethyl group and $n_{24}$ is 3, then $R_{24}^1$ cannot be phenyl; as well as the pharmaceutically acceptable salts described in EP 502536.

XXV—TP 9201

A composition comprising a cyclic RGD containing a peptide having a hydrophobic entity adjacent to the carboxyl end of the said RGD sequence.

XXVI—RO 44-9883 or one of its analogues of formula:

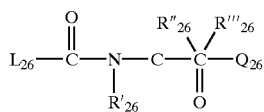

(XXVI)

in which $L_{26}$ is a group of formula

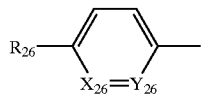

or alternatively represents $R°_{26}$—NH(CH$_2$)$t_{26}$, $R_{26}$, is an amidino or a guanidino, $X_{26}$ or $Y_{26}$ being CH and the other CH or N, $R'_{26}$ being hydrogen or an amidino, $t_{26}$ being an integer between 2 and 6, $R'_{26}$, $R''_{26}$ and $R'''_{26}$ being independently hydrogen or the conventional substituents of the nitrogen atom of the α-amino acids, or the conventional side chains of the α-amino acids, it being possible for the hydroxyl or carboxyl groups present in R', R" and R'" to be etherified, esterified or in the form of amides, and it being possible for the amino groups present. in R', R" and R'" to be; alkanoylated or aroylated;

$Q_{26}$ is a group of formula

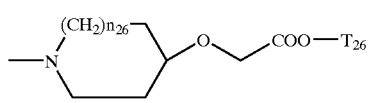

(Q$_{26}^1$)

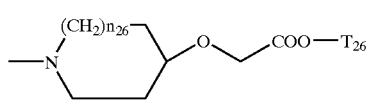

(Q$_{26}^2$)

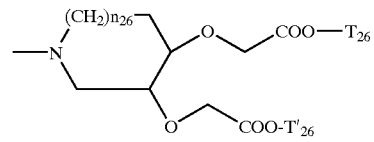

(Q$_{26}^3$)

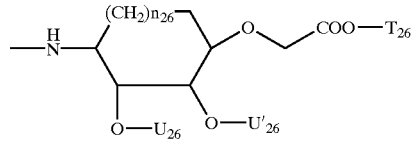

(Q$_{26}^4$)

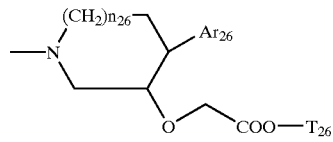

(Q$_{26}^5$)

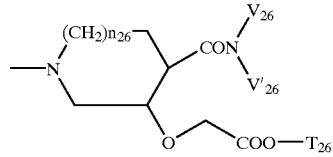

(Q$_{26}^6$)

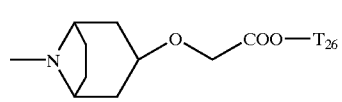

(Q$_{26}^7$)

—N(V'$_{28}$)(CH$_2$)$_{\nu 26}$—C(V"$_{26}$, V'"$_{26}$)CH$_2$OCH$_2$COO—T$_{26}$  (Q$_{26}^8$)

or when R'$_{26}$ and R"$_{26}$ together form a ring with the N or C atom to which they are bonded, $Q_{26}$ may also represent the group:

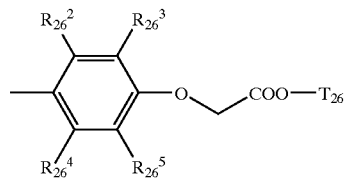

(Q$_{26}^9$)

$n_{26}$ represents 0 or 1, $v_{26}$ is an integer between 0 and 3, $T_{23}$ and $T'_{26}$ are hydrogen or represent a lower alkyl group or a lower phenylalkyl which is cleavable under physiological conditions;

$V_{26}$ to $V'''_{26}$ is hydrogen or a lower alkyl group;

$U_{26}$ and $U'_{26}$ are hydrogen, a $(C_1-C_6)$alkanoyl or aroyl, $Ar_{26}$ is an aryl and $R_{26}^2$ to $R_{26}^5$ are hydrogen, a lower alkyl, a lower alkoxy, a halogen or a group-OCH$_2$COO—T'$_{26}$ or $R_{26}^2$ and $R_{26}^3$ together form with the phenyl group to which they are bonded a 1-naphthyl group as well as their hydrates and solvates and their pharmaceutically acceptable salts, as described in EP 505 868.

XXVII—RO 43-8857 and its analogues of formula:

$R^1_{27}$—A$_{27}$—(W$_{27}$)$_{a27}$—X$_{27}$—(CH$_2$)$_{b27}$—Y$_{27})_{c27}$—B$_{27}$—Z$_{27}$—
COOR$_{27}$  (XXVII)

in which:

$A_{27}$ denotes a residue

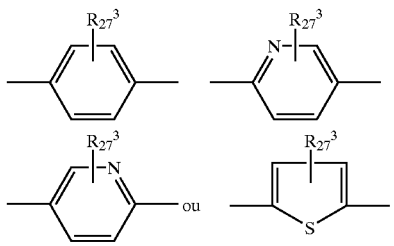

$B_{27}$ denotes a residue

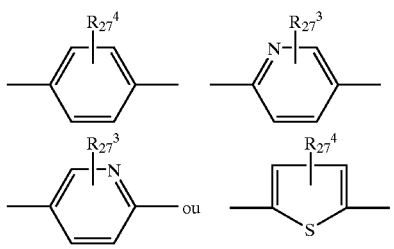

and $W_{27}$ represents —CH$_2$—, —CH$_2$CH$_2$—, —CH=CH—, —CH=CH—CH$_2$—, —(CH$_2$)$_3$—, —CH$_2$CH(CH$_3$)—, —COCH$_2$—, —CH(OH)CH$_2$— or —CH$_2$COCH$_2$;

—$X_{27}$ represents —CONR$_{27}^2$—, —NR$_{27}^2$CO—, —SO$_2$NR$_{27}^2$— or —NR$_{27}^2$SO$_2$—;

$Y_{27}$ represents —CH$_2$CH$_2$—, —CH$_2$CH$_2$O—, —OCH$_2$—, —CH(CH$_3$)CH$_2$—, —CH=CH—, —CH$_2$—CH=CH—, —C(Q$_{27}^1$)(Q$_{27}^2$)—CO(CH$_2$)$d_{27}$—, —CH$_2$—, —CH$_2$CH$_2$CH$_2$—, —CH(CH$_3$)CH$_2$CH$_2$—, —CH$_2$COCH$_2$—, —C(Q$_{27}^1$)(Q$_{27}^2$)—CH(OH)—, —C(Q$_{27}^1$)(Q$_{27}^2$)—CH(SSCH$_3$)—, —CH(CH$_2$OH)CH$_2$— or —CH(COOR$_{27}$)CH$_2$—, whereas the carbonyl groups may also be present in the form of oxime, oxime ether, ketal or thioketal or enol ether groups and the hydroxyl. groups in the form of lower alkyl ether groups, di(lower alkyl)amino(lower alkyl) ether groups or in the form of lower alkylcarboxylic acid ester groups, $Z_{27}$ denotes —OCH$_2$—, —NR$_{27}^6$CH$_2$—, —CH$_2$CH$_2$—, —CH(CH$_3$)CH$_2$—, —CH$_2$—, —CH=CH— or —C(CH$_3$)=CH—;

$R_{27}$ represents hydrogen or a lower alkyl, phenyl or phenyl(lower alkyl) group;

$Q_{27}^1$ and $Q_{27}^2$ are hydrogen or an alkyl group or form with the carbon atom to which they are bonded a 3- to 6-membered saturated ring;

$R_{27}^1$ denotes an amidino or guanidino group;

$R_{27}^2$ denotes hydrogen or a lower alkyl group, a phenyl (lower alkyl) group, a phenyl(lower alkyl) group substituted in the phenyl portion with amino, anidino or —COOR$_{27}$ radicals, or a —CH$_2$COOR$_{27}$ or Y$_{27}$—B$_{27}$—Z$_{27}$—COOR$_{27}$ residue;

$R_{27}^3$ represents hydrogen or a lower alkyl, lower alkoxy, halogen, lower alkoxycarbonyl, amino, lower alkylamino, di(lower alkyl)amino or amidino group;

$R_{27}^4$ represents hydrogen or a lower alkyl, lower alkoxy, halogen, lower alkoxycarbonyl, amino, lower alkylamino, di(lower alkyl)amino group or a —Z$_{27}$—COOR$_{27}$ or —CH=CH—(CH$_2$)n$_{27}$COOR$_{27}$ residue;

$R_{27}^6$ denotes hydrogen or a lower alkyl or benzyl group;

$n_{27}$ represents an integer from 0 to 4;

$a_{27}$, $c_{27}$ and $d_{27}$ are independent of each other, 0 or 1; and $b_{27}$ denotes an integer from 0 to 2, whereas nevertheless $a_{27}$ and $b_{27}$ should be equal to 0 when C$_{27}$ is 1 and C$_{27}$ should be equal to 0 when $a_{27}$ or $b_{27}$ is different from 0;

as well as their physiologically acceptable salts, as described in EP 381 033.

XXVIII—RO 43-5054 and its acetic acid derivatives of formula:

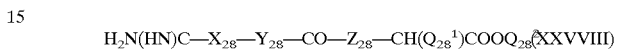

$$H_2N(HN)C—X_{28}—Y_{28}—CO—Z_{28}—CH(Q_{28}^1)COOQ_{28}^2 \quad (XXVVIII)$$

in which:

$Q_{28}^1$ is hydrogen, a methyl or phenyl, $Q_{28}^2$ is hydrogen, a phenyl(lower alkyl), or a lower alkyl which is cleavable under physiological conditions;

$X_{28}$ is a 1,4-phenylene; 2,5-pyridylene or 3,6-pyridylene or a 1,4-piperidinylene group attached to the group Y by the carbon atom at the 4-position;

$Y_{28}$ is a group of formula —(CH$_2$)$_{0-2}$—CONHCH(Q$_{28}^3$)(CH$_2$)$_{1-3}$, —CONHCH$_2$CH(Q$_{28}^4$)—, —(CH$_2$)$_2$NHCOCH$_2$—, —NHCO(CH$_2$)$_3$—,

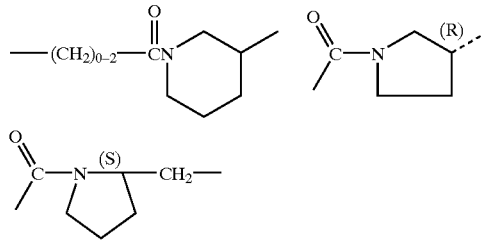

$Q_{28}^3$ is a hydrogen, a methyl, a phenyl, a —COOH, —COO(lower alkyl), a CONH(CH$_2$)$_2$—COOH or a —CONH—(CH$_2$)$_2$—COO(lower alkyl), $Q_{28}^4$ is a hydrogen, a methyl or a phenyl, $Z_{28}$ is a 1,4-piperazinylene group, a 1,4-piperidinylene group bonded to the CO group via the nitrogen atom at the 1-position or a group of formula —NHCH(R$_{28}^1$)— or —NHCH(COR$_{28}^2$)— in which:

$R_{28}^1$ is a hydrogen, a methyl, a phenyl or a —COO(lower alkyl), $R_{28}^2$ is an α-amino acid residue bonded via its amino group or the ester or amide of the latter, or a group of formula —NHCH$_2$CH$_2$—Ar$_{28}$ or —CO—R$_{28}^2$ represents a carbamoyl group which is optionally mono- or dialkylated by a lower alkyl group or a pyrrolidinocarbonyl or piperidinocarbonyl group;

$Ar_{28}$ is a phenyl or a phenyl substituted with a lower alkyl, a lower alkoxy, a —COOH, a —COO(lower alkyl), a —O(CH$_2$)$_{1-4}$—COOH, a —O(CH$_2$)$_{1-4}$—COO(lower alkyl), a —CONH$_2$, a —CONH(lower alkyl), or a —CON(lower alkyl)$_2$, a pyrrolidinocarbonyl or a piperidinocarbonyl, as well as their hydrates, their solvates and their pharmaceutically acceptable salts, as described in EP 445796.

XXIX—MK 0383 and its analogues of formula:

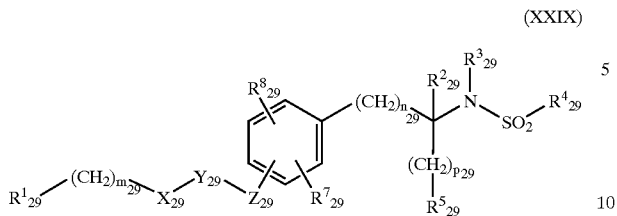

(XXIX)

in which:
$R^1_{28}$ is a heterocyclic ring consisting of 4 to 8 members containing 1, 2, 3 or 4 heteroatoms in which the said heteroatoms are N, O or S and the said heterocyclic ring is optionally substituted on any atom with $R^6_{29}$ or $R^7_{29}$; $NR^6_{29}R^7_{29}$;

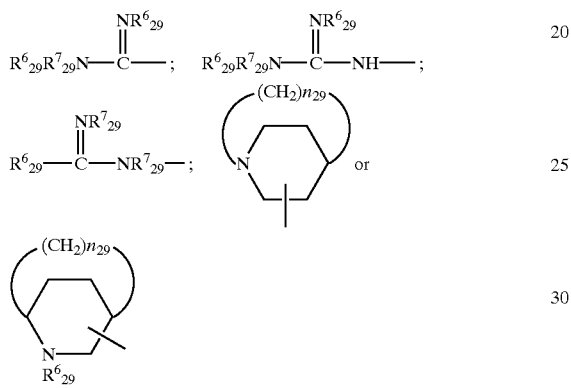

in which:
$R^6_{29}$ and $R^7_{29}$ are independently a hydrogen, and a $(C_1-C_{10})$alkyl group or a substituted or unsubstituted cycloalkyl group in which the said substituents are $(C_1-C_{10})$alkoxy, $(C_1-C_{10})$alkoxyalkyl, $(C_1-C_{10})$alkoxyalkyloxy, $(C_1-C_{10})$alkoxycarbonyl, $(C_1-C_{10})$alkylcarbonyl, $(C_4-C_{10})$aralkylcarbonyl, $(C_1-C_{10})$alkylthiocarbonyl, $(C_1-C_{10})$aralkylthiocarbonyl, thiocarbonyl, $(C_1-C_{10})$alkoxythioalkyl, aryl, a saturated heterocycle with 5 or 6 saturated members containing 1, 2, 3 or 4 heteroatoms in which the said heteroatoms are selected from the group consisting of N, O and S, $(C_1-C_4)$alkanoylamino, $(C_1-C_6)$alkoxycarbonyl-$(C_0-C_6)$alkylamino, $(C_1-C_{10})$alkylsulphonylamino, $(C_4-C_{10})$aralkylsulphonylamino, $(C_4-C_{10})$aralkyl, $(C_1-C_{10})$alkaryl, $(C_1-C_{10})$alkylthio, $(C_4-C_{10})$aralkylthio, $(C_1-C_{10})$alkylsulphinyl, $(C_4-C_{10})$aralkylsulphinyl, $(C_1-C_{10})$alkylsulphonyl, $(C_4-C_{10})$aralkylsulphonyl, aminosulphonyl, $(C_1-C_{10})$alkylaminosulphonyl, $(C_4-C_{10})$aralkylsulphonylamino, oxo, thioxo, an unsubstituted, a monosubstituted or a disubstituted 1-ethynyl, 2-ethynyl or 3-propenyl group, in which the said substituents are selected from the group consisting of hydrogen, $(C_1-C_{10})$alkyl and $(C_4-C_{10})$aralkyl, carboxyl, hydroxyl, amino, $(C_1-C_6)$alkylamino, $(C_1-C_6)$dialkylamino, halogen in which the halogen is selected from F, Cl, Br, and I, nitro, and cyano; it being possible for the nitrogen atom of the said heterocyclic ring to be, in addition, substituted with an additional $R^6_{29}$ group to form a quaternary ammonium ion;

$R^2_{29}$ and $R^3_{29}$ are independently hydrogen, aryl or a $(C_1-C_{10})$alkyl or cycloalkyl group, unsubstituted or substituted, in which the said substituent is a $(C_1-C_{10})$alkoxyalkyl, aryl, a saturated heterocycle having from 4 to 8 members containing 1, 2, 3 or 4 heteroatoms in which the heteroatoms are selected from the groups consisting of N, O and S, $(C_4-C_{10})$aralkyl, $(C_1-C_{10})$alkaryl, $(C_1-C_{10})$alkylthio, $(C_4-C_{10})$aralkylthio, $(C_1-C_{10})$alkylsulphinyl, $(C_4-C_{10})$aralkylsulphinyl, $(C_1-C_{10})$alkylsulphonyl, $(C_4-C_{10})$aralkylsulphonyl, carboxyl, $(C_1-C_{10})$alkylcarbonyl, $(C_1-C_{10})$alkylthiocarbonyl, $(C_4-C_{10})$aralkylcarbonyl, $(C_4-C_{10})$aralkylthiocarbonyl, $(C_1-C_6)$alkoxycarbonyl, $(C_4-C_{10})$aralkoxycarbonyl, $(C_1-C_6)$alkoxy, $(C_1-C_6)$alkoxycarbonyl-$(C_1-C_4)$alkyl, $(C_4-C_{10})$aralkoxycarbonyl-$(C_1-C_4)$alkyl, $(C_4-C_{10})$aralkoxy, $(C_1-C_6)$alkylamino, $(C_1-C_{12})$dialkylamino, $(C_1-C_6)$alkanoylamino, $(C_4-C_{10})$aralkanoylamino, $(C_4-C_{10})$aralkylamino, $R^4_{29}$ is aryl, $(C_1-C_{10})$alkyl or cycloalkyl, $(C_4-C_{10})$aralkyl, $(C_1-C_{10})$alkoxyalkyl, $(C_1-C_{10})$alkaryl, $(C_1-C_{10})$alkylthioalkyl, $(C_1-C_{10})$alkoxythioalkyl, $(C_1-C_{10})$alkylamino, $(C_4-C_{10})$aralkylamino, $(C_1-C_{10})$alkanoylamino, $(C_4-C_{10})$aralkanoylamino, $(C_1-C_{10})$alkanoyl, $(C_1-C_{10})$aralkanoyl, and a substituted or unsubstituted $(C_1-C_{10})$carboxyalkyl in which the said substituent is aryl, $(C_1-C_{10})$aralkyl; it being possible for each of the substituents of $R^4_{29}$ to be, in addition, substituted with a substituent selected from the group defined for $R^6_{29}$;

$R^5_{29}$ is a saturated or unsaturated 4- to 8-membered heterocyclic ring containing 1, 2, 3 or 4 heteroatoms selected from N, O and S or

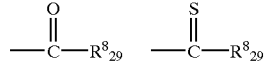

in which:
$R^8_{29}$ is hydroxyl, $(C_1-C_{10})$alkyloxy, $(C_1-C_{10})$alkaryloxy, $(C_4-C_{10})$aralkyloxy, $(C_4-C_{10})$aralkylcarbonyloxy, $(C_1-C_{10})$alkoxyalkyloxy, $(C_1-C_{10})$alkoxyalkylcarbonyloxy, $(C_1-C_{10})$alkoxycarbonylalkyl, $(C_1-C_{10})$alkylcarbonyloxyalkoxy, or an L- or a D-amino acid bonded via an amide bond, or an amino acid bonded via an amide bond and in which the carboxylic acid functional group of the said amino acid is optionally esterified with a $(C_1-C_6)$alkyl or a $(C_4-C_{10})$aralkyl, or $R^8_{29}$ represents:

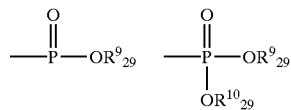

in which:
$R^9_{29}$ and $R^{10}_{29}$ are selected from the group consisting of hydrogen, $(C_1-C_{10})$alkyl and $(C_4-C_{10})$aralkyl;
$X_{29}$ and $Y_{29}$ are optional substituents which, when present, represent $NR^6_{29}$, O, S, SO, $SO_2$,

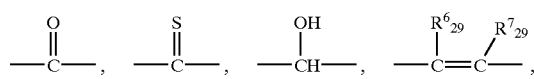

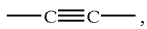

-continued a ring having from 4 to 8 members containing 0, 1, 2, 3 or 4 heteroatoms selected from N, O and S, in which the said ring is independently substituted on any of its atoms with $R^6_{29}$, an aryl, or

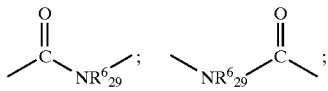

or $-NR_{629}SO_2-$; $-SO_2NR^6_{29}-$;

$Z_{29}$ is an optional substituent which, when present, is independently selected from the substituents defined for $X_{29}$ and $Y_{29}$;

$m_{29}$ is an integer from 0 to 10;

$n_{29}$ is an integer from 0 to 10; and $p_{29}$ is an integer from 0 to 3;

as well as its pharmaceutically acceptable salts, as described in EP 478 363.

XXX—Tirofiban or one of its analogues of formula;

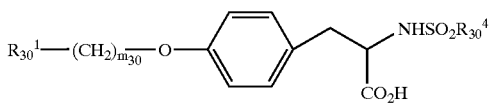

(XXX)

in which:

$R_{30}^1$ is a 4-piperidinyl or a 4-pyridinyl;

$m_{30}$ is an integer from 2 to 6; and $R_{30}^4$ is an aryl, a $(C_1-C_{10})$alkyl or a $(C_4-C_{10})$aralkyl as described in U.S. Pat. No. 5,206,373.

XXXI—DUP 728 and its analogues of formula:

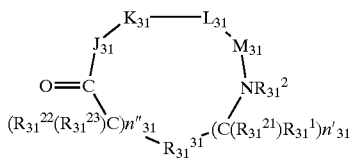

(XXXI)

$R_{31}^{31}$ is a saturated, partially saturated or aromatic carbocyclic $C_6-C_{14}$ ring, substituted with 0 to 2 substituents $R_{31}^{10}$; or $n''_{31}$ and $n'_{31}$ are independently an integer from 0 to 3;

$R_{31}^1$ and $R_{31}^{22}$ are independently selected from the following groups:

hydrogen, $(C_1-C_8)$alkyl substituted with 0 to 2 substituents, $R_{31}^{11}$, a $(C_2-C_8)$alkenyl substituted with 0 to 2 substituents $R_{31}^{11}$, a $(C_2-C_6)$alkynyl substituted with 0 to 2 substituents $R_{31}^{11}$, a $(C_3-C_8)$cycloalkyl substituted with 0 to 2 substituents $R_{31}^{11}$, a $(C_6-C_{10})$bicycloalkyl substituted with 0 to 2 substituents $R_{31\ 1}^{11}$ an aryl substituted with 0 to 2 substituents $R_{31}^{12}$, a heterocycle substituted with 0 to 2 substituents $R_{31}^{12}$, composed of 5 to 10 atoms including from 1 to 3 heteroatoms of nitrogen, S or O, =O, F, Cl, Br, I, $-CF_3$, $-CN$, $-CO_2R_{31}^{13}$, $-C(=O)R_{31}^{13}$, $-C(=O)NR_{31}^{13}R_{31}^{14}$, $-CHO$, $-CH_2OR_{31}^{13}$, $-OC(=O)R_{31}^{13}$, $-OC(=O)OR_{31}^{13}$, $-OR_{31}^{13}$, $-OC(=O)NR_{31}^{13}R_{31}^{14}$, $-NR_{3114}C(=O)R_{31}^{13}$, $-NR_{31}^{14}C(=O)OR_{31}^{13}$, $-NR_{31}^{13}C(=O)NR_{31}^{13}R_{31}^{14}$, $-NR_{31}^{14}SO_2NR_{31}^{13}R_{31}^{14}$, $-NR_{31}^{14}SO_2R_{31}^{13}$, $-SO_3H$, $-SO_2R_{31}^{13}$, $-SR_{31}^{13}$, $-S(=O)R_{31}^{13}$, $-SO_2NR_{31}^{13}R_{31}^{14}$, $-NR_{31}^{13}R_{31}^{14}$, $-NHC(=NH)NHR_{31}^{13}$, $-C(=NH)NHR_{31}^{13}$, $=NOR_{31}^{14}$, $NO_2$, $-C(=O)NHOR_{31}^{13}$, $-C(=O)NHNR_{31}^{13}R_{31}^{14}$, oxime, boronic acid, $-OCH_2CO_2H$, 2-(1-morpholino)ethoxy;

or $R_{31}^1$ and $R_{31}^{21}$ may bond together to form a carbocyclic ring having from 5 to 7 members, substituted with 0 to 2 substituents $R_{31}^{12}$;

or $R_{31}^{22}$ and $R_{31}^{23}$ may bond together to form a carbocyclic ring having from 5 to 7 members, substituted with 0 to 2 substituents $R_{3112}$;

or $R_{31}^1$ and $R_{31}^2$, when $R_{31}^{21}$ is hydrogen, may become bonded to form a carbocyclic ring having from 5 to 8 members, substituted with 0 to 2 substituents $R_{31}^{12}$;

$R_{31}^{11}$ may be selected from one of the following groups: =O, F, Cl, Br, I, $-CF_3$, $-CN$, $-CO_2R_{31}^{13}$, $-C(=O)R_{31}^{13}$, $-C(=O)NR_{31}^{13}R_{31}^{14}$, $-OHO$, $-CH_2OR_{31}^{13}$, $-OC(=O)R_{31}^{13}$, $-OC(=O)OR_{31}^{13}$, $-OR_{31}^{13}$, $-OC(=O)NR_{31}^{13}R_{31}^{14}$, $-NR_{31}^{14}C(=O)R_{31}^{13}$, $-NR_{31}^{14}C(=O)OR_{31}^{13}$, $-NR_{31}^{13}C(=O)NR_{31}^{13}R_{31}^{14}$, $-NR_{31}^{14}SO_2NR_{31}^{13}R_{31}^{14}$, $-NR_{31}^{14}SO_2R_{31}^{13}$, $-SO_3H$, $-SO_2R_{31}^{13}$, $SR_{31}^{13}$, $-S(=O)R_{31}^{13}$, $-SO_2NR_{31}^{13}R_{31}^{14}$, $-NR_{31}^{13}R_{31}^{14}$, $-NHC(=NH)NHR_{31}^{13}$, $-C(=NH)NR_{31}^{13}$, $=NOR_{31}^{14}$, $NO_2$, $-C(=O)NHOR_{31}^{13}$, $-C(=O)NHNR_{31}^{13}R_{31}^{14}$, oxime, boronic acid, $-OCH_2CO_2H$, 2-(1-morpholino)ethoxy, a $(C_1-C_5)$alkyl, a $(C_2-C_4)$alkenyl, a $(C_3-C_6)$cycloalkyl, a $(C_3-C_6)$cycloalkylmethyl, a $(C_2-C_6)$alkoxyalkyl, a $(C_3-C_6)$cycloalkoxy, a $(C_1-C_4)$alkyl, (substituted with an $-NR_{31}^{13}R_{3114}$, a $-CF_3$, an $NO_2$, an $SO_2R_{31}^{13a}$ or an $-S(=O)R_{31}^{13a}$, an aryl substituted with 0 to 2 substituents $R_{31}^{12}$, a heterocyclic ring substituted with 0 to 2 substituents $R_{31}^{12}$, composed of 5 to 10 atoms including from 1 to 3 heteroatoms of nitrogen, oxygen or sulphur;

$R_{31}^{12}$ is selected from one or more of the following groups:

a phenyl, benzyl, phenethyl, phenoxy, benzyloxy, halogen, hydroxyl, nitro, cyano, $(C_1-C_5)$alkyl, $(C_3-C_6)$cycloalkyl, $(C_3-C_6)$cycloalkylmethyl, $(C_7-C_{10})$aryl-alkyl, $(C_1-C_4)$alkoxy, $-CO_2R_{31}^{13}$, $-C(=O)NHOR_{31}^{13}$, $-O(=O)NHNR_{31}^{13}R_{31}^{14}$, oxime, boronic acid, $(C_3-C_6)$cycloalkoxy, $-OC(=O)R_{31}^{13}$, $-C(=O)R_{31}^{13}$, $-OC(=O)OR_{31}^{13}$, $-OR_{31}^{13}$, $-CH_2OR_{31}^{13}$, $-NR_{31}^{13}R_{31}^{14}$, $-OC(=O)NR_{31}^{13}R_{31}^{14}$, $-NR_{31}^{14}C(=O)R_{31}^{13}$, $-NR_{31}^{14}C(=O)OR_{31}^{13}$, $-NR_{31}^{13}C(=O)NR_{31}^{13}R_{31}^{14}$, $-NR_{31}^{14}SO_2NR_{31}^{13}R_{31}^{14}$, $-NR_{31}^{14}SO_2R_{31}^{13a}$, $-SO_3H$, $-SO_2R_{31}^{13a}$, $-S(=O)R_{31}^{13a}$, $-SR_{31}^{13}$, $-SO_2NR_{31}^{13}R_{31}^{14}$, $(C_2-C_6)$alkoxyalkyl, $(C_1-C_4)$hydroxyalkyl, methylenedioxy, ethylenedioxy, $(C_1-C_4)$haloalkyl, $(C_1-C_4)$haloalkoxy, $(C_1-C_4)$alkoxycarbonyl, $(C_1-C_4)$alkylcarbonyloxy, $(C_1-C_4)$alkylcarbonyl, $(C_1-C_4)$alkylcarbonylamino, $-OCH_2CO_2H$, 2-(1-morpholino)ethoxy, $(C_1-C_4)$alkyl (substituted with an $-NR_{31}^{13}R_{31}^{14}$, $CF_3$, $NO_2$ or with an $-S(=O)R_{31}^{13a}$);

$R_{31}{}^{13}$ is H, $(C_1-C_7)$alkyl, an aryl, —$((C_{1-6})$alkyl)aryl or a $(C_3-C_6)$alkoxyalkyl;

$R_{31}{}^{13a}$ is a $(C_1-C_7)$alkyl, an aryl, a —$((C_1-C_6)$alkyl)aryl, or a $(C_3-C_6)$alkoxyalkyl;

$R_{31}{}^{14}$ is OH, H, $(C_1-C_4)$ alkyl, or benzyl, $R_{31}{}^{21}$ and $R_{31}{}^{23}$ are independently selected from: hydrogen; $(C_1-C_4)$alkyl optionally substituted with a halogen; a $(C_1-C_2)$alkoxy; a benzyl;

$R_{31}{}^2$ is H or a $(C_1-C_8)$alkyl;

$R_{31}{}^{10}$ is independently selected from one or more of the following groups:

a phenyl, benzyl, phenethyl, phenoxy, benzyloxy, halogen, hydroxyl, nitro, cyano, $(C_1-C_5)$alkyl, $(C_3-C_6)$cycloalkyl, $(C_3-C_6)$cycloalkylmethyl, $(C_7-C_{10})$ arylalkyl, $(C_1-C_4)$alkoxy, —$CO_2R_{31}{}^{13}$, —$C(=O)NHOR_{31}{}^{13}$, —$C(=O)NHNR_{31}{}^{13}R_{31}{}^{14}$, oxime, boronic acid, $(C_3-C_6)$cycloalkoxy, —$OC(=O)R_{31}{}^{13}$, —$C(=O)R_{31}{}^{13}$, —$OC(=O)OR_{31}{}^{13}$, —$OR_{31}{}^{13}$, —$CH_2OR_{31}{}^{13}$, —$NR_{31}{}^{13}R_{31}{}^{14}$, —$NR_{31}{}^{13}C(=O)NR_{31}{}^{13}R_{31}{}^{14}$, —$NR_{31}{}^{14}SO_2NR_{31}{}^{13}R_{31}{}^{13}R_{31}{}^{14}$, —$NR_{31}{}^{14}SO_2R_{31}{}^{13a}$, —$SO_2R_{31}{}^{13a}$, —$SO(=O)R_{31}{}^{13a}$, —$SR_{31}{}^{13}$, —$SO_2NR_{31}{}^{13}R_{31}{}^{14}$, $(C_2-C_6)$alkoxyalkyl, $(C_1-C_4)$hydroxyalkyl, methylenedioxy, ethylenedioxy, $(C_1-C_4)$haloalkyl, $(C_1-C_4)$haloalkoxy, $(C_{1-C4})$alkoxycarbonyl, $(C_1-C_4)$alkylcarbonyloxy, $(C_1-C_4)$alkylcarbonyl, $(C_1-C_4)$alkylcarbonylamino, —$OCH_2CO_2H$, 2-(1-morpholino)ethoxy, $(C_1-C_4)$alkyl (substituted with an —$NR_{31}{}^{13}R_{31}{}^{14}$, $CF_3$, $NO_3$ or with an —$S(=O)R_{31}{}^{13a}$);

$J_{31}$ is β-Ala or the residue of an amino acid of the L isomer or of the D isomer of structure —$N(R_{31}{}^3)C(R_{31}{}^4)(R_{31}{}^5)C(=O)$—, in which:

$R_{31}{}^3$ is H or a $(C_1-C_8)$alkyl;
$R_{31}{}^4$ is H or a $(C_1-C_3)$alkyl;
$R_{31}{}^5$ is hydrogen, a $(C_1-C_8)$alkyl substituted with from 0 to 2 substituents $R_{31}{}^{11}$, a $(C_2-C_8)$alkenyl substituted with from 0 to 2 substituents $R_{31}{}^{11}$, a $(C_2-C_8)$alkynyl substituted with from 0 to 2 substituents $R_{31}{}^{11}$, a $(C_3-C_8)$cycloalkynyl substituted with from 0 to 2 substituents $R_{31}{}^{11}$, a $(C_6-C_{10})$bicycloalkyl substituted with from 0 to 2 substituents $R_{31}{}^{11}$, an aryl substituted with from 0 to 2 substituents $R_{31}{}^{12}$, a heterocyclic ring substituted with from 0 to 2 substituents $R_{31}{}^{12}$, composed of 5 to 10 atoms including from 1 to 3 heteroatoms N, S or O, or $R_{31}{}^5$ represents ↑O, F, Cl, Br, I, —$CF_3$, —CN, —$CO_2R_{31}{}^{13}$, —$C(=O)R_{31}{}^{13}$, —$C(-OC(=O)OR_{31}{}^{13}$, —$CH_2OR_{31}{}^{13}$, —$OC(=O)NR_{31}{}^{13}$, —$OC(=O)OR_{31}{}^{13}$, —$OR_{31}{}^{13}$, —$OC(=O)NR_{31}{}^{14}$, —$NR^{3114}$ $C(=O)R_{31}{}^{13}$, —$NR_{31}{}^{14}C(=O)OR_{31}{}^{13}$, —$NR_{31}{}^{13}C(=O)NR_{31}{}^{13}R_{31}{}^{14}$, —$NR_{31}{}^{14}SO_2NR_{31}{}^{13}R_{31}{}^{14}$, —$NR_{31}{}^{14}SO_2R_{31}{}^{13a}$, —$SO_3H$, —$SO_2R_{31}{}^{13a}$, —$SR_{31}{}^{13}$, —$S(=O)R_{31}{}^{13a}$, —$SO_2NR_{31}{}^{13}R_{31}{}^{14}$, —$NR_{31}{}^{13}R_{31}{}^{14}$, —$NHC(=NH)NHR_{31}{}^{13}$, —$C(=NH)NHR_{31}{}^{13}$, =$NOR_{31}{}^{14}$, $NO_2$, —$C(=O)NHOR_{31}{}^{13}$, —$C(=O)NHR_{31}{}^{13}R_{31}{}^{14}$, oxime, boronic acid, —$OCH_2CO_2H$, 2-(1-morpholino)ethoxy, —$SC(=NH)NHR_{31}{}^{13}$, $N_3$, —$Si(CH_3)_3$, $((C_1-C_5)$alkyl)$NHR_{31}{}^{16}$; $((C_0-C_6)$alkyl)$X_{31}$;

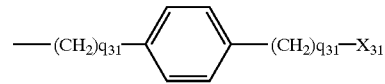

in which $q_{31}$ is independently 0 or 1,

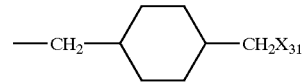

—$(CH_2)_{m_{31}}S(CH_2)_2X_{31}$, in which $m_{31}$ is 1 or 2; and in which $X_{31}$ is defined below;

$R_{31}{}^3$ and $R_{31}{}^4$ may also form together

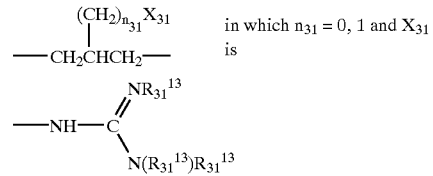

in which $n_{31}$ = 0, 1 and $X_{31}$ is $R_{31}{}^3$ and $R_{31}{}^5$, may also form together —$(CH_2)_{t_{31}}$— (with $t_{31}$=2–4) or —$CH_2SC(CH_3)_2$—or $R_{31}{}^4$ and $R_{31}{}^5$ may also form together —$(CH_2)_{u_{31}}$ in which $u_{31}$ is 2–5;

$R_{31}{}^{16}$ is selected from an amine protecting group, 1 to 2 amino acids, 1 to 2 amino acids substituted with an amine protecting group;

$K_{31}$ is an amino acid of the L isomer or of the D isomer of structure —$N(R_{31}{}^6)CH(R_{31}{}^7)C(=O)$— in which $R_{31}{}^6$ is H, or a $(C_1-C_6)$alkyl, $R_{31}{}^7$ is selected from —$((C_1-C_7)$alkyl)$X_{31}$,

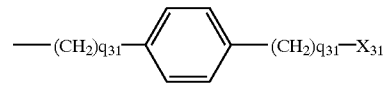

in which $q_{31}$ is independently 0 or 1;

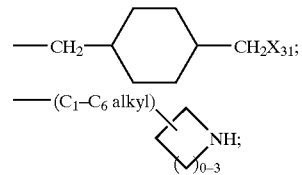

—$(CH_2)_{m_{31}}O$—$((C_1-C_4)$alkyl)—$X_{31}$ in which $m_{31}$ is 1 or 2;

—$(CH_2)_{m_{31}}S((C_1-C_4)$alkyl)—$X_{31}$ in which $m3_1$ is 1 or 2 and $X_{31}$ is selected from

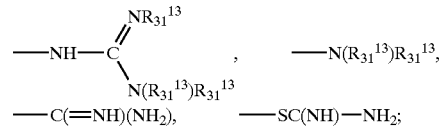

$R_{31}{}^6$ and $R_{31}{}^7$ may also form together

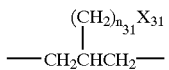

in which n=0, 1 and $x_{31}$ is

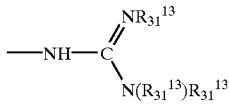

$L_{31}$ is —$Y_{31}(CH_2)v_{31}C(=O)$— in which $Y_{31}$ is NH, N(($C_1$-$C_3$)alkyl)), O or S; and $v_{31}$ is 1 or 2;

$M_{31}$ is the residue of an amino acid of the L isomer or of the D isomer of structure —$NR_{31}{}^{17}$—$CH(R_{31}{}^8)C(=O)$— in which $R_{31}{}^{17}$ is H, ($C_1$-$C_3$)alkyl;

$R_{31}{}^8$ is —$CH_2CO_2R_{31}{}^{13}$, —$CH_2SO_3R_{31}{}^{13a}$, —$CH(CH_3)CO_2R_{31}{}^{13}$, —$SO_2NR_{31}{}^{13}R_{31}{}^{14}$, —$CH_2$—boronic acid, —$CH_2$—tetrazole, —$NHSO_2CF_3$, $CONHNHSO_2CF_3$, —$PO(OR_{31}{}^{13})_2$, —$PO(OR_{31}{}^{13})R_{31}{}^{13}$, —$CONHOR_{31}{}^{13}$—, —$SO_2NH$-heteroaryl, —$CH_2SO_2NH$-heteroaryl, —$SO_2NHCOR_{31}{}^{13}$, —$CH_2SO_2NHCOR_{31}{}^{13}$, —$CONHSO_2R_{31}{}^{13a}$, —$CH_2CONHSO_2R_{31}{}^{13a}$, —$NHSO_2NHCOR_{31}{}^{13a}$, —$NHCONHSO_2R_{31}{}^{13}$, —$SO_2NHCONR_{13}{}^{31}$, or its pharmaceutically acceptable salts, as described in WO 93/07170.

XXXII—L 70-3014 or one of its analogues of formula:

(XXXII)

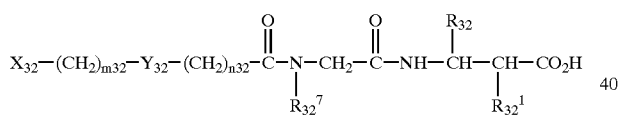

in which:

$X_{32}$ is

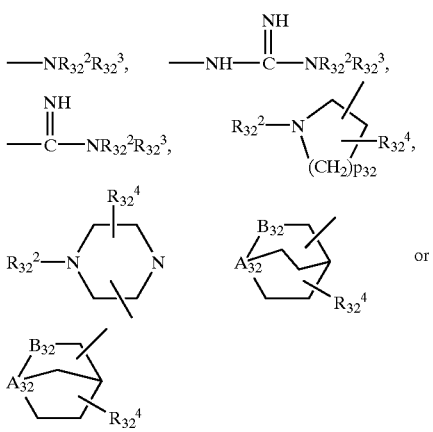

in which $A_{32}$=N and $B_{32}$=.$CH_2$— or $A_{32}$=>CH— and $B_{32}$=N—$R^2{}_{32}$;

$Y_{32}$ is

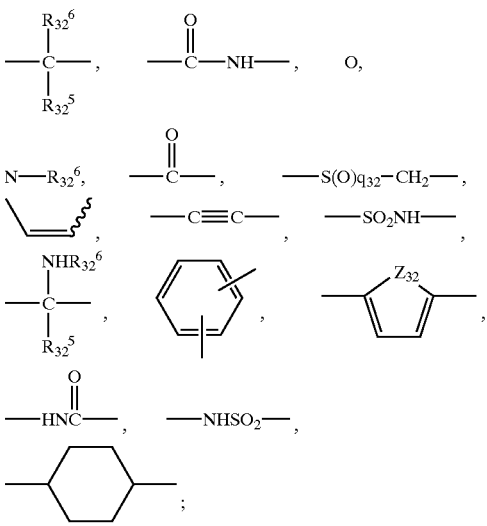

$R_{32}$ and $R_{32}$ are independently
hydrogen,
an aryl in which the aryl is defined as a 5- or 6-membered mono- or polycyclic aromatic ring containing 0, 1, 2, 3 or 4 heteroatoms selected from nitrogen, oxygen and sulphur, the said aryl being unsubstituted or substituted with one or more groups selected from a hydroxyl, a halogen, a cyano, a trifluoromethyl, a ($C_1$-$C_3$)alkoxy, a ($C_1$-$C_5$)alkylcarbonyloxy, a ($C_1$-$C_5$)alkoxycarbonyl, a ($C_1$-$C_5$)alkyl, an amino ($C_1$-$C_5$)alkyl, a hydroxycarbonyl($C_0$-$C_5$)alkyl or a hydroxycarbonyl ($C_1$-$C_5$)alkoxy; a ($C_1$-$C_5$)alkyl unsubstituted or substituted with one or more groups selected from halogen, hydroxyl, ($C_1$-$C_5$)alkylcarbonylamino, aryl ($C_1$-$C_5$)alkylcarbonylamino, aryloxy, ($C_1$-$C_{10}$) alkoxy, ($C_1$-$C_5$)alkoxycarbonyl, ($C_0$-$C_5$) alkylaminocarbonyl, ($C_1$-$C_5$)alkylcarbonyloxy, ($C_3$-$C_8$)cycloalkyl, aryl, oxo, amino, ($C_1$-$C_6$)alkyl, ($C_1$-$C_3$)alkylamino, amino($C_1$-$C_3$)alkyl, aryl ($C_0$-$C_5$)alkylaminocarbonyl, ethylene, phenyl ($C_1$-$C_3$)alkylamino, aminocarbonyl($C_0$-$C_4$)alkyl and hydroxycarbonyl($C_0$-$C_5$)alkyl;

it being understood that the carbon atom to which $R_{32}$ and $R_{32}{}^1$ are linked carries only one heteroatom;

$R_{32}{}^2$, $R_{32}{}^3$ and $R_{32}{}^4$ are independently hydrogen, cyano, a ($C_1$-$C_{12}$)alkyl unsubstituted or substituted with one or more ($C_1$-$C_6$)alkyl or aryl($C_0$-$C_4$)alkyl groups, it being understood that when $R_{32}{}^2$ and $R_{32}{}^3$ are independently a cyano, $X_{32}$ is 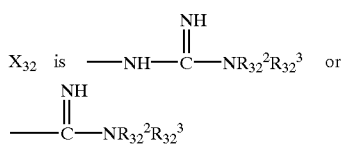

$R_{32}{}^6$ is hydrogen, a hydroxylcarbonyl, a hydroxyl, an amino or a ($C_1$-$C_6$)alkyl unsubstituted or substituted with one or more groups selected from a ($C_1$-$C_6$)alkyl, a ($C_1$-$C_5$)alkoxy, a ($C_1$-$C_5$)alkoxycarbonyl, a hydroxycarbonyl ($C_0$-$C_4$)alkyl, an aryl, an amino($C_1$-$C_4$)alkyl, an arylaminocarbonyl($C_0$-$C_4$)alkyl, a ($C_1$-$C_4$)

alkylsulphonyl, a phenyl($C_0$–$C_4$)alkylsulphonyl, a hydroxyl and an amino, with the proviso that when $R^6{}_{32}$ is hydroxyl or amino, $R^5{}_{32}$ is not bonded to a carbon atom carrying a heteroatom;

$R_{32}{}^6$ is hydrogen or ($C_1$–$C_{12}$)alkyl unsubstituted or substituted with one or more groups ($C_1$–$C_6$)alkyl, aryl ($C_0$–$C_3$)alkyl, ($C_1$–$C_4$)alkyloxycarbonyl, an aryl ($C_1$–$C_4$)alkyloxycarbonyl, a ($C_1$–$C_4$)alkylaminocarbonyl, an aryl($C_1$–$C_4$)alkylaminocarbonyl, a ($C_2$–$C_5$) alkoxy, an oxycarbonyl ($C_2$–$C_5$ )alkyl, or an aminocarbonyl($C_2$–$C_5$)alkyl;

$R_{32}{}^7$ is hydrogen, an aryl, a ($C_3$–$C_7$)cycloalkyl, or a ($C_1$–$C_{12}$)alkyl unsubstituted or substituted with one or more ($C_1$–$C_5$)alkyl, ($C_3$–$C_7$)cycloalkyl, hydroxyl, hydroxycarbonyl, aminocarbonyl, oxo or aryl groups;

$m_{32}$ is an integer from 1 to 10;

$n_{32}$ is an integer from 0 to 9;

$q_{32}$ is an integer from 0 to 2;

$p_{32}$ is an integer from 1 to 6;

$z_{32}$ is O, N, S;

or their pharmaceutically acceptable salts or their optical isomers, as described in EP 478362.

XXXIII—SC 54684 or one of its derivatives of formula:

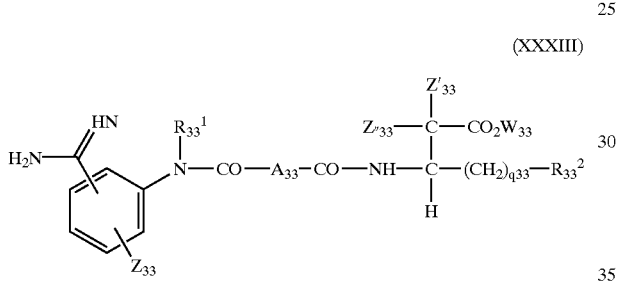

(XXXIII)

in which:

$R_{33}{}^1$ is selected from the group consisting of a hydrogen, lower alkyl radicals, lower alkenyl radicals, hydrocarbon-containing aromatic radicals, hydrocarbon-containing alicyclic radicals, benzyl radicals, phenethyl radicals, it being possible for the said radicals to be substituted with a halogen, a lower alkoxy, a hydroxyl or a lower alkyl;

$R_{33}{}^2$ is selected from the group consisting of a hydrogen, lower alkyl radicals, lower alkenyl radicals, lower alkynyl radicals, hydrocarbon-containing aromatic radicals, hydrocarbon-containing alicyclic radicals, benzyl radicals, phenethyl radicals, it being possible for the said radicals to be substituted with a halogen, a lower alkoxy, a hydroxyl or a lower alkyl;

$A_{33}$ is selected from the group consisting of lower alkylene radicals, lower alkenylene radicals, lower alkynylene radicals, and alicyclic divalent radicals, the said radicals being optionally substituted with a hydroxyl, a lower alkoxy, a lower alkyl, a halogen, an alkoxycarbonylalkyl, an amino, an alkylamino, a dialkylamino, an acylamino, an alkylthio, a sulphonyl, or aromatic hydrocarbon-containing radicals optionally substituted with a halogen, nitro, lower alkoxy or lower alkyl;

$W_{33}$ is selected from the group consisting of hydrogen, lower alkyl radicals, lower alkenyl radicals, lower alkynyl radicals and alicyclic hydrocarbon radicals or hydrocarbon-containing aromatic radicals, the said radicals being optionally substituted with a hydroxyl, a lower alkoxy, a lower alkyl, a halogen, a nitro, an amino, an acyloxy, a phenyl or a naphthyl, it being possible for the phenyl and naphthyl groups to be optionally substituted with a halogen, a nitro, a lower alkoxy or a lower alkyl;

$Z_{33}$, $Z'_{33}$ and $Z''_{33}$ are independently selected from the group consisting of hydrogen, lower alkyl radicals, halogen, alkoxy, cyano, sulphonyl, carboxyl, alkoxycarbonyl, and hydroxyl radicals;

$q_{33}$ is an integer between 0 and 6; and with the proviso that when $A_{33}$ is a trimethylene and $q_{33}$ is 0, then $R_{33}{}^2$ cannot be hydrogen, a methyl radical or a phenyl radical, and also that when $A_{33}$ is a trimethylene, and $q_{33}$ is 1, then $R_{33}{}^2$ cannot be a hydrogen, as described in WO 93/07867.

XXXIV—SC 58053 or one of its analogues of formula:

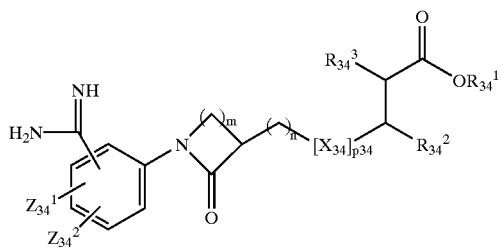

(XXXIV)

or one of its pharmaceutically acceptable salts, in which $Z^1{}_{34}$ and $Z_{34}$ are independently selected from the group consisting of ($C_1$–$C_6$)alkyl, hydroxyl, halogen or ($C_1$–$C_6$)alkoxy;

$R^1{}_{34}$ is selected from the group consisting of hydrogen, lower ($C_1$–$C_6$)alkyl, lower ($C_2$–$C_6$)alkenyl, lower ($C_2$–$C_6$)alkynyl, alkyloxycarbonyloxyalkyl, ($C_3$–$C_6$) cycloalkyl and aryl optionally substituted with a hydroxyl, a lower($C_1$–$C_6$)alkoxy, a lower($C_1$–$C_6$)alkyl, a halogen, nitro, amino, acyloxy, phenyl or naphthyl;

$R^2{}_{34}$ is selected from the group consisting of a hydrogen, a lower($C_1$–$C_6$)alkyl, a lower($C_2$–$C_6$)alkenyl, a lower ($C_2$–$C_6$)alkynyl, a cycloalkyl, an aryl, monocyclic, bicyclic or tricyclic heterocyclic radicals comprising 1 to 3 heteroatoms independently selected from oxygen, nitrogen and sulphur, the said radicals being optionally substituted with one or more radicals selected from. the group consisting of a hydroxyl, a lower($C_1$–$C_6$)alkoxy, a lower($C_1$–$C_6$)alkyl, a halogen, nitro, cyano, azido, ureido, ureylene, carboxyl, carbonyl derivatives, trifluoromethyl, acyloxy, alkylthio, arylthio, alkylsulphinyl, arylsulphinyl, alkylsulphonyl, arylsulphonyl, amino, alkylamino, trialkylsilyl, aminosulphonyl, dialkylamino, alkanoylamino, aroylamino, phenyl and naphthyl;

$R^3{}_{34}$ is selected from the group consisting of hydrogen, ($C_1$–$C_6$)alkyl, ($C_1$–$C_6$)alkoxy, halogen, amino, monoalkylamino, dialkylamino, acylamino, alkylsulphonylamino, arylsulphonylamino, hydroxyl, alkoxycarbonyl and alkoxycarbonylalkyl;

$X_{34}$ is selected from the group consisting of

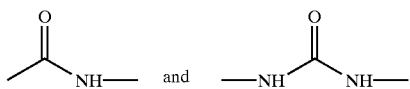

$m_{34}$ is an integer from 1 to 4;
$n_{34}$ is an integer from 0 to 4; and
$p_{34}$ is 0 or 1 in which $n_{34}$ and $p_{34}$ are not both equal to 0; as described in WO 94/22820.

XXXV—GR 144053 or one of its analogues of formula:

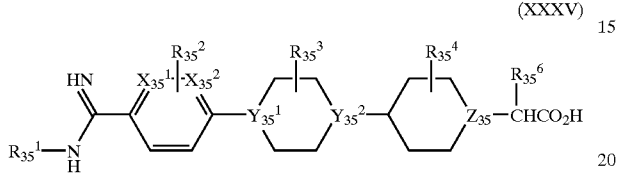

(XXXV)

in which
$X^1_{35}$ and $Y^1_{35}$, which are identical or different, represent CH or N;
$X^2_{35}$ represents CH, but when $X^1_{35}$ represents CH, it may also represent N;
$Y^2_{35}$ represents N, but when $Y^1_{35}$ represents N, it may also represent CH;
$Z_{35}$ represents N or $N^4R^5_{35}$;
$R^1_{35}$ represents a hydrogen atom or a hydroxyl, a $(C_1-C_4)$ alkyl or a 2,2,2-trifluoroethyl group;
$R^2_{35}$ represents a hydrogen atom but when $X^1_{35}$ and $X^2_{35}$ both represent CH, it may also represent a fluorine, chlorine or bromine atom or a $(C_1-C_4)$alkyl group;
$R^3_{35}$ represents a hydrogen atom but when $Y^1_{35}$ and $Y^2_{35}$ both represent N, it may also represent a $(C_1-C_4)$alkyl group or a hydroxymethyl group;
$R^4_{35}$ represents a hydrogen atom, or when $Z_{35}$ represents N, $R^4_{35}$ may also represent a $(C_1-C_4)$alkyl group;
$R^5_{35}$ represents a $(C_1-C_4)$alkyl group or a phenyl group;
$R^6_{35}$ represents a hydrogen atom or a $(C_1-C_4)$alkyl group;
as well as its pharmaceutically acceptable derivatives, salts and solvates, as described in EP 542363.

XXXVI—BIBU 104 and its analogues of formula:

(XXXVI)

in which:
$A_{36}$ represents a 4- to 7-membered iminocyclic alkylene group optionally substituted with $R_{36}^1$, $R_{36}^2$ and $R_{36}^3$ groups, in which an ethylene group may be substituted with an ethenylene group or a methylene group may be substituted with a carbonyl group;
$R_{36}^1$ represents an aryl group or an optionally mono- or polyunsaturated alkyl group of 1 to 6 carbon atoms, which may be substituted with one or two aryl groups, with a cycloalkyl, alkylthio, alkylsulphinyl, alkylsulphonyl, alkylcarbonyl, aralkylcarbonyl, arylcarbonyl, $R_{36}^4$—O—CO— or $(R_{36}^5)_2$NCO— group or a group $R_{36}^6$CO or with a bi- or tricyclic aryl group, which may be completely or partially hydrogenated, it being understood that the unsaturated alkyl group cannot be directly linked to the endocyclic nitrogen atom of the radical $A_{36}$ by a triple bond and that a double bond can only be linked to the endocyclic nitrogen atom when a carbonyl group is contiguous to the double bond, or as long as $R_{36}^1$ is not attached to the nitrogen atom of the radical $A_{36}$ when $A_{36}$ represents a lactam ring, $R_{36}^1$ represents a carbonyl group, which is substituted with an alkyl, aralkyl, aryl, $(R_{36}^5)_2N$, $R_{36}^4OCO$, $(R_{36}^5)NCO$, alkoxy, aralkoxy, alkylcarbonyl-$NR_{36}^5$-alkyl, aralkylcarbonyl-$NR_{36}^5$-alkyl, arylcarbonyl-$NR_{36}^5$-alkyl, $R_{36}^4O$-alkyl, $(R_{36}^5)_2$N-alkyl, alkyl-$SO_2$-$NR_{36}^5$-alkyl, aralkyl-$SO_2$-$NR_{36}^5$-alkyl or aryl-$SO_2$-$NR_{36}^5$-alkyl group;

a $(C_1-C_6)$alkyl group, substituted with $R_{36}^6$, with one or two hydroxyl groups, with an alkoxy, aryloxy, aralkoxy, arylthio, aralkylthio, arylsulphinyl, aralkylsulphinyl, arylsulphonyl, aralkylsulphonyl, $N(R_{36}^5)_2$-sulphonyl, $R_{36}^6$-sulphonyl, $(R_{36}^5)_2N$, alkylcarbonyl-$NR_{36}^5$, arylcarbonyl-$NR_{36}^5$, aralkylcarbonyl-$NR_{36}^5$, alkylsulphonyl-$NR_{36}^5$, arylsulphonyl-$NR_{36}^5$, aralkylsulphonyl-$NR_{36}^5$, $(R_{36}^5)_2$N—CO—$NR_{36}^5$— group or a group $(R_{36}^5)_2$N—$SO_2$—$NR_{36}^5$, it being understood, that when $R_{36}^1$ is linked to the endocyclic nitrogen atom of the radical $A_{36}$, the substituents of the alkyl group are present only from the 2-position onwards, or when the radical $R_{36}^1$ is not linked to a carbon atom adjacent to the endocyclic nitrogen atom and when the radical $R_{36}^1$ is not linked to an unsaturated carbon atom of the radical $A_{36}$, $R_{36}^1$ may also represent a hydroxyl, alkylcarbonyl-$NR_{36}^5$, arylcarbonyl-$NR_{36}^5$, aralkylcarbonyl-$NR_{36}^5$, alkylsulphonyl-$NR_{36}^5$, arylsulphonyl-$NR_{36}^5$, aralkylsulphonyl-$NR_{36}^5$, $(R_{36}^5)_2$N—CO—$NR_{36}^5$ or $(R_{36}^5)_2$N—$SO_2$—$NR_{36}^5$ group, or as long as $R_{36}^1$ is not linked to the nitrogen atom of the radical $A_{36}$, when $A_{36}$ represents a lactam ring and is not linked to the carbon atom adjacent to the nitrogen atom, $R_{36}^1$ may also represent an alkylsulphonyl, arylsulphonyl, aralkylsulphonyl or $(R_{36}^5)_2$N—$SO_2$ group, or when the radical $R_{36}^1$ is not linked to the endocyclic atom of the radical $A_{36}$ or to a carbon atom adjacent to the endocyclic nitrogen atom of the radical $A_{36}$ or to an unsaturated carbon atom of the radical $A_{36}$, $R_{36}^1$ may represent an alkoxy, aryloxy, aralkoxy, alkylthio, arylthio, aralkylthio, alkylsulphinyl, arylsulphinyl or aralkylsulphinyl group, or when $R_{36}^1$ is not linked to the endocyclic nitrogen atom of the radical $A_{36}$, $R_{36}^1$ may represent a carboxyl group, in which,
$R_{36}^4$ and $R_{36}^5$ which are identical or different, represent a hydrogen atom, an alkyl, aralkyl, aryl or alkoxyalkyl group, it being understood that the alkoxy group cannot be present on the same carbon atom as the carbonyloxy or carbonylamino group, and $R_{36}^6$ is a 5- to 7-membered alkylenimino group linked by the nitrogen, in which a methylene group at the 3-position or at the 4-position may be replaced with an S, a sulphinyl, sulphonyl, imino, alkylimino, aralkylimino, arylimino, formylimino, alkanoylimino, aralkanoylimino, arylcarbonylimino, $(R_{36}^6)$2N-carbonylimino, alkylsulphonylimino, aralkylsulphonylimino or arylsulphonylimino, or an $(R_{36}^5)_2$N-sulphonylimino group, and when $R_{36}^6$ is not linked to a carbonyl group or to a sulphonyl group, the said methylene group can also be replaced at the 2-position by a carbonyl group or at the 4-position by a sulphur atom, it being understood that $R_{36}5$ is as defined above and that the alkanoyl portion contains from 1 to 4 carbon atoms, $R_{36}^2$ and $R_{36}^3$, which are identical or different, represent alkyl, aryl or aralkyl, $B_{36}$ represents a cyano group or a nitro group, an amino group or an aminoalkyl of 1 to 6 carbon atoms optionally substituted on the nitrogen atom with one or two alkyl groups of 1 to 5 carbon atoms or with an aralkyl group, an amidino, guanidino, amidinoalkyl or guanidinoalkyl group optionally substituted with 1, 2 or 3($C_1$–$C_5$)alkyl groups or with an aralkyl group, in which the alkyl portion contains each time from 1 to 6 carbon atoms and in which two nitrogen atoms of an amidino group or of a guanidino group may also form together an alkylene chain of 2 to 4 carbon atoms, it being understood that a nitrogen atom in the abovementioned groups may also be substituted with a cyano, hydroxyl, alkoxy, amino, arylcarbonyl, aryloxycarbonyl, or aralkoxycarbonyl group or with an alkoxycarbonyl group of 2 to 6 carbon atoms as long as it does not exist in the form of an ammonium, or an ammonium or ammonioalkyl group of 1 to 6 carbon atoms substituted with 3 alkyl groups of 1 to 3 carbon atoms, $E_{36}$, which is linked to a carbon atom of the group $Y_{36}$ or of the group $A_{36}$ and which has at the very minimum between itself and the first nitrogen atom of $B_{36}$ at least 10 bonds, is a vinyl, a hydroxymethyl, a bis(hydroxycarbonyl)methyl, a bis(alkoxycarbonyl)methyl, a CN, a sulpho, a phosphono, an O-alkylphosphono or a 5-tetrazolyl, a carbonyl (substituted with a ($C_1$–$C_7$)alkoxy, with $NH_2$, OH, aralkoxy, heteroarylalkoxy, aminoalkoxy or with an aminocarbonylalkoxy, in which the amino groups are themselves optionally mono- or disubstituted with alkyl, aryl or aralkyl, or an alkyleneiminoalkoxy containing from 5 to 7 members (in which one of the $CH_2$ groups of the 5- to 7-membered alkylenimino ring is optionally replaced by a carbonyl, it being also possible for a group at the 4-position to be replaced by an oxygen atom, a sulphur atom, SO, imino, alkylimino, aralkylimino or arylimino, or at the 2- or 4-position by an $SO_2$), with the proviso that if $B_{36}$ is linked via a nitrogen atom to an aryl group of $X_{36}$, E36 cannot be a vinyl linked by a methylene to the cyclic nitrogen of $A_{36}$ if $A_{36}$ is a pyrrolidine;

$X_{36}$ is a group of formula —$X_{36}^1$—$X_{36}^2$—$X_{36}^3$—$X_{36}^4$—$X_{36}^5$— in which $X_{36}$ is bonded to the radical $A_{36}$ and $X_{36}^5$ is bonded to the radical $B_{36}$, and represents a bond, an optionally mono- or polyunsaturated alkylene group, or an optionally mono- or polyunsaturated arylene group, it being understood that between the alkylene group and the adjacent group $X_{36}^2$, there may also be in addition an oxygen atom or a sulphur atom or an SO, $SO_2$, $NR_{36}^7$, CO, CO—$NR_{36}^8$, $NR_{36}^8$—CO, $SO_2$—$NR_{36}^8$, $NR_{36}^8$—$SO_2$, $NR_{36}^8$—CO—$NR_{36}^8$ or $NR_{36}^8$—$SO_2$—$NR_{36}^8$ group, or alternatively when the radical $X_{36}^1$ is not linked to the endocyclic nitrogen atom of the radical $A_{36}$, when $A_{36}$ represents a lactam ring, $X_{36}^1$ represents a carbonyl, alkylenecarbonyl, CONR$_{36}^8$ or CO—O group and, in the case where the group $X_{36}^1$ is not bonded to a carbon atom adjacent to the endocyclic nitrogen atom or to the endocyclic nitrogen atom of the radical $A_{36}$, when $A_{36}$ represents a lactam ring, $X_{36}^1$ represents an $SO_2$ group or an $SO_2$—$NR_{36}^8$ group, or when the radical $X_{36}^1$ is not linked to a carbon atom adjacent to the endocyclic nitrogen atom of the radical $A_{36}$, $X_{36}^1$ may also represent an oxygen atom, an $NR_{36}^7$, $NR_{36}^8$—CO or $NR_{36}^8$—$SO_2$ group, or when the group $X_{36}^1$ is not linked to the endocyclic nitrogen atom or to the carbon atom adjacent to the endocyclic nitrogen atom of the radical $A_{36}$, $X_{36}^1$ may also represent a sulphur atom or a sulphinyl group, it being understood that $R_{36}^7$ represents a hydrogen atom, an alkyl, aralkyl, aryl, alkylcarbonyl, aralkylcarbonyl, arylcarbonyl, alkylsulphonyl, arylsulphonyl, aralkylsulphonyl, aminocarbonyl or aminosulphonyl group, it being possible for the abovementioned amino groups to be mono- or disubstituted with identical or different substituents selected from the alkyl, aralkyl or aryl groups, and $R_{36}^8$ represents a hydrogen atom, an alkyl, aryl or aralkyl group, $X_{36}^2$ represents a fluorenylene ring whose methylene group may be replaced by a carbonyl or hydroxymethylere group, or an arylene ring, in which two carbon atoms adjacent to the arylene ring may be optionally attached by a propylene, propenylene, butylene, butenylene, butadienylene, pentylene, pentenylene or pentadienylene bridge, a naphthalene ring completely or partially hydrogenated on the two rings or a tricyclic arylene ring optionally completely or partially hydrogenated, it being understood that in these cyclic systems, a methylene group may be replaced by a carbonyl or hydroxymethylene group, an optionally mono- or polyunsaturated cycloalkylene group, an optionally mono- or polyunsaturated bicycloalkylene group of 6 to 12 carbon atoms or an optionally mono- or polyunsaturated spiroalkylene group of 8 to 12 carbon atoms, which may further carry 1 to 3 alkyl substituents, an alkylene group of 1 to 8 carbon atoms, which may be mono- or polyunsaturated, it being understood, however, that a double bond or a triple bond is not adjacent to a heteroatom, $X_{36}^3$ represents a bond, an alkylene group of 1 to 7 carbon atoms, which may be mono- or polyunsaturated, it being understood that a double or triple bond cannot be adjacent to a triple bond of the radical $X_{36}^2$, or a hydroxyalkylene group, or when $X_{36}^3$ is not immediately after an optionally substituted amino group, a trialkylammonium group or a nitro group or after a triple bond of the radical $B_{36}$, $X_{36}^3$ may also represent a CO, CONR$_{36}^8$ or $NR_{36}^8$CO group, it being understood that the latter is not directly bonded to an aliphatic double or triple bond of the radical $X_{36}^2$, or when $X_{36}^3$ is not immediately after a heteroatom or an unsaturated carbon atom of the radical $B_{36}$, $X_{36}^3$ may also represent an $SO_2$ group, or alternatively when $X_{36}^2$ does not contain an aliphatic double or triple bond at its end, and when $X_{36}^3$ does not immediately follow a heteroatom or an unsaturated carbon atom of the radical $B_{36}$, $X_{36}^3$ may also represent an oxygen atom or a sulphur atom, an SO, $NR_{36}^7$, $NR_{36}^3SO_2$ or $SO_2NR_{36}^8$ group, it being understood that $R_{36}^7$ and $R_{36}^8$ are as defined above, $X_{36}^4$ represents a bond, an arylene group, in which two adjacent carbon atoms may be linked by a propylene, propenylene, butylene, butenylene, butadienylene, pentylene, pentenylene or pentatienylene bridge, a cycloalkylene group or a bicycloalkylene group of 6 to 12 carbon atoms and $X_{36}^6$ represents a bond, an alkylene group, which may be mono- or polyunsaturated, it being understood that a double or triple bond cannot be bonded to a heteroatom of the radical $B_{36}$ or of the radical $X_{36}^3$ or to a terminal triple bond of the radical $X_{36}^3$, if $X_{36}^4$ represents a bond, a CO-alkylene group or if $X_{36}^6$ is not immediately after an optionally alkylated amino group, a trialkylammonium group or a nitro group or after a triple bond of the radical $B_{36}$, then $X_{36}^5$ may also represent CO, $CONR^8_{36}$ or $NR^8_{36}$—CO, it being understood that the latter is not directly bonded to an oxygen atom or a sulphur atom or to a carbonyl group of the radical $X_{36}^3$ or to a double or a triple bond, or alternatively when the alkylene group of the radical $B_{36}$ follows $X_{36}^5$ and that $X_{36}^5$ is not immediately adjacent to an oxygen atom or to a sulphur atom or to a carbonyl group of the radical $X_{36}^3$ or to a double or triple bond, $X_{36}^5$ may also represent an $NR^8_{36}$—$SO_2$, $SO_2NR^8_{36}$ or $SO_2$ group, or when $X_{36}^5$ is not immediately adjacent to a heteroatom or to a CO group of the radical $X_{36}^3$ or to a double or triple bond, $X_{36}^5$ may also represent an O-alkylene, S-alkylene or SO-alkylene group, it being understood that a heteroatom of the radical $B_{36}$ is not present on the same carbon atom as an oxygen atom, a sulphur atom or an SO group and that the radicals $R^7_{36}$ and $R^8_{36}$ are as defined above and $Y_{36}$ is a group of formula:

$$-Y_{36}^1-Y_{36}^2-Y_{36}^3-,$$

in which $Y_{36}^1$ is bonded to the group $A_{36}$ and $Y_{36}^3$ is bonded to the group $E_{36}$ and $Y_{36}^1$ represents a bond, an alkylene group, which may be mono- or polyunsaturated, it being understood, however, that a triple bond of the alkyl group is not directly bonded to the endocyclic nitrogen atom of the radical $A_{36}$ and that a double bond may be bonded to the endocyclic nitrogen atom only if it is followed by a carbonyl group, a hydroxyalkylene group in which the hydroxyl group is not carried by the carbon atom which is bonded to the endocyclic nitrogen of the radical $A_{36}$ if $Y_{36}^1$ is linked to the endocyclic nitrogen, a CO group or a CO—$NR^8_{36}$ group, as long as they are not directly bonded to the endocyclic nitrogen atom of the radical $A_{36}$ when the latter represents a lactam ring, or when $Y_{36}^1$ is not linked to a carbon atom adjacent to the endocyclic nitrogen atom of the radical $A_{36}$ and is not on the endocyclic nitrogen atom of the radical $A_{36}$, when $A_{36}$ represents a lactam ring, $Y_{36}^1$ also represents an $SO_2$ group or an $SO_2$—$NR^8_{36}$ group, or when $Y_{36}^1$ is not linked to the endocyclic nitrogen atom or to a carbon atom adjacent to the endocyclic nitrogen atom or to an unsaturated carbon atom of the radical $A_{36}$, $Y_{36}^1$ may also represent an oxygen atom, a sulphur atom or an SO, $NR^7_{36}$ or $NR^8_{36}$—$SO_2$ group, it being understood that $R^7_{36}$ and $R^8_{36}$ are as defined above, $Y_{36}^2$ represents a bond, an alkylene group, which may be mono- or polyunsaturated, it being understood, however, that a double bond or a triple bond cannot be adjacent to a heteroatom or to a triple bond of the radical $Y_{36}^1$, an arylene group, or when $Y_{36}^1$ does not end with an oxygen atom or a sulphur atom or a triple bond or a CO group, $Y_{36}^2$ represents CO, $SO_2$ or $CONR^8_{36}$, or when $Y_{36}^1$ does not end with an oxygen atom, a sulphur atom or a sulphinyl group or a double or triple bond, $Y_{36}^2$ represents an $NR^7_{36}$ group, or when $Y_{36}^1$ does not end with a heteroatom, a double or triple bond or a CO group, $Y_{36}^2$ represents an oxygen atom, a sulphur atom or an SO group or an O—CO group, or alternatively when $Y_{36}^1$ does not end with a double or triple bond, with an oxygen atom or with a sulphur atom or with a CO group, $Y_{36}^2$ represents an $NR^8_{36}$—$SO_2$ or $SO_2$—$NR^8_{36}$ group, it being understood that $R^7_{36}$ and $R^8_{36}$ are as defined above, $Y_{36}^3$ represents a bond, an arylene, alkylene-arylene, alkylenoxy-arylene, alkylenesulphenyl-arylene, alkylenesulphinyl-arylene, alkylenesulphonyl-arylene, alkylene-$NR^8_{36}$-arylene, alkylene-N(alkylcarbonyl)arylene, alkylene-N(aralkylcarbonyl)arylene, alkylene-N(arylcarbonyl)arylene, alkylene-$NR^8_{36}$-carbonyl-arylene, alkylenecarbonyl-$NR^8_{36}$-arylene, bisarylene, alkylene-bisarylene or alkylenoxy-bisarylene group, it being understood that $R^8_{36}$ is as defined above, or alternatively when $Y_{36}^1$ and $Y_{36}^2$ each represent a bond, $Y_{36}^3$ may represent hydroxyalkylene, $N(R^5_{36})_2$-alkylene, alkylcarbonyl-$NR^8_{36}$-alkylene, aralkylcarbonyl-$NR^8_{36}$-alkylene, arylcarbonyl-$NR^8_{36}$-alkylene, alkylsulphonyl-$NR^8_{36}$-alkylene or arylsulphonyl-$NR^8_{36}$-alkylene, it being understood that when $Y_{36}$ is linked to the endocyclic nitrogen atom of the radical $A_{36}$, a hydroxyl, $NR^8_{36}$ or $N(R^5_{36})_2$ group is not linked to the carbon atom of the radical $A_{36}$ bonded to the endocyclic nitrogen atom and it being understood that $R_{36}^5$, and $R^8_{36}$ are as defined above, the alkylene, alkyl, alkoxy, cycloalkyl, cycloalkylene, aryl and arylene groups being as defined in application EP 483 667, it being understood that aryl and arylene groups are understood to mean mono-, bi- or tricyclic aromatic groups, which may be monosubstituted with an aryl, aralkyl or nitro group and/or which may be mono-, di- or trisubstituted with a fluorine, chlorine or bromine atom, with an alkyl group of 1 to 5 carbon atoms, with a hydroxyl, alkoxy, aralkoxy, trifluoromethyl, mercapto, alkylthio, alkylsulphinyl, alkylsulphonyl, amino, alkylamino, dialkylamino, alkylcarbonylamino, aralkylcarbonylamino, arylcarbonylamino, alkoxycarbonylamino, alkylsulphonylamino, arylsulphonylamino, N-alkylcarbonylalkylamino, N-aralkylcarbonylalkylamino, N-arylcarbonylalkylamino, N-alkoxycarbonylalkylamino, N-alkylsulphonylalkylamino, N-arylsulphonylalkylamino, cyano, aminocarbonyl, alkylaminocarbonyl, dialkylaminocarbonyl, aminosulphonyl, alkylaminosulphonyl, dialkylaminosulphonyl, alkylcarbonyl, aralkylcarbonyl, arylcarbonyl, carboxyl, sulpho, alkoxycarbonyl, aminocarbonylamino, N-aminocarbonylalkylamino or aminoalkyl, the substituents being identical or different and it being possible for the amino groups of the abovementioned aminocarbonylamino, N-aminocarbonylalkylamino or aminoalkyl groups to be, in addition, mono- or disubstituted with an alkyl or aralkyl group, their geometric isomers and the addition salts, as described in EP 483 667.

XXXVII—BIBU 129 or a cyclic urea derivative of formula:

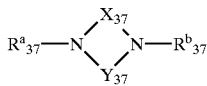

(XXXVII)

in which $X_{37}$ is a carbimino optionally substituted with alkyl, aralkyl, aryl, heteroaryl, or cyano, CO, CS, SO or $SO_2$;

$Y_{37}$ is
- (a) a straight $(C_2-C_4)$alkylene, or an alkenylene optionally substituted with $R^c_{37}$ and/or $R^d_{37}$, and in which each carbon atom is substituted with one or two identical or different substituents selected from F, Cl, Br, alkyl, $CF_3$, aralkyl, aryl, heteroaryl and alkylcarbonyl, and in which also one or two $CH_2$ may be replaced by CO;
- (b) 1,2-$(C_4-C_7)$cycloalkylene optionally substituted with $R^c_{37}$ and/or $R^d_{37}$;
- (c) 1,2-$(C_4-C_7)$ cycloalkenylene;
- (d) 1,2-phenylene in which 1 or 2 CH are optionally substituted with N or 1 or 2 CH=CH with a $CONR^1_{37}$, the said 1,2-phenylene being optionally substituted on its carbon backbone with F, Cl, Br, $(C_1-C_4)$alkyl, $CF_3$, OH, alkoxy, alkylthio, alkylsulphinyl, alkylsulphonyl, alkylcarbonyl, arylcarbonyl, alkoxycarbonyl, COOH, $NO_2$, $(R^1_{37})_2N$, $(R^1_{37})_2NCO$, $(R^1_{37})_2NSO_2$, or with $R^1_{37}NH$ (it being possible for —$R_{37}^1$ itself to be substituted with an alkylcarbonyl, arylcarbonyl, aralkylcarbonyl, hetero arylcarbonyl, alkylsulphonyl, aralkylsulphonyl, or arylsulphonyl)

$R^1_{37}$ is a hydrogen atom, an alkyl, an aralkyl, an aryl or a heteroaryl;

or $Y_{37}$ is
- (e) CONH, NHCO, CH=N or N=CH, optionally substituted with $R^c_{37}$ or $R^d_{37}$; a radical from $R^a_{37}$ to $R^d_{37}$ is $A_{37}$—$B_{37}$—$C_{37}$— in which:

$A_{37}$ is a $(C_1-C_5)$aminoalkyl, $NH_2$, amidino, guanidino (for each of these groups, one or two hydrogen atoms bonded to a nitrogen atom may be replaced with a $(C_1-C_4)$alkyl or a hydrogen atom bonded to a nitrogen may be replaced with a $(C_2-C_5)$alkoxycarbonyl, alkylcarbonyl, arylcarbonyl, aryloxycarbonyl or aralkylcarbonyl); CN, cyano $(C_1-C_4)$alkyl; or provided that $A_{37}$ is linked to an N atom of $B_{37}$ or $C_{37}$ not forming part of a lactam ring, then $A_{37}$ may also represent H or alkyl;

$B_{37}$ is a bond, an alkylene, or an alkenylene; a phenylene (optionally substituted with one or two identical or different substituents selected from F, Cl, Br, $(C_1-C_4)$ alkyl, $CF_3$, OH, alkoxy, alkylthio, alkylsulphinyl, alkylsulphonyl, $(R^1_{37})_2N$, $(R^1_{37})_2NCO$, $(R^1_{37})_2NSO_2$, $NO_2$ or $R^1_{37}NH$, it being possible for the latter to be substituted as defined above;

a pyridinylene, pyrimidinylene, pyrazinylene, pyridazylene or triazinylene ring (all optionally substituted on the carbon-containing backbone with an alkyl; it being possible for one or two —CH=N— groups of these rings to be replaced with $CONR^1_{37}$, it being possible for a nitrogen atom to be attached to the radical $C_{37}$ instead of $R_{37}^1$ as long as the latter is not bonded to a heteroatom or to a carbonyl group of the radical $B_{37}$), a cyclopropylene, (optionally substituted with an alkyl, aralkyl or aryl);

$(C_4-C_5)$cycloalkylene (optionally substituted like cyclopropylene and it being possible for a CH of the cycloalkylene to be replaced with a nitrogen atom, it being possible for a $CH_2$ adjacent to the nitrogen atom to be replaced in addition with CO);

a $(C_6-C_7)$cycloalkylene (optionally substituted like the cyclopropylene and in which 1 or 2 CH (at the 1–4 position) may be replaced with a nitrogen atom, it being possible for a $CH_2$ adjacent to the nitrogen atom to be in addition replaced with a carbonyl group);

or a biphenylene (optionally substituted with one or two F, Cl, Br, alkyl, $CF_3$, OH, alkoxy, alkylthio, alkylsulphinyl, alkylsulphonyl, alkylcarbonyl-$NR_{37}^1$ or alkylsulphonyl-$NR^1_{37}$);

$C_{37}$ is an alkylene or an alkenylene (optionally substituted with OH, alkoxy or $N(R^1_{37})_2$); alkylenecarbonyl (bonded to $B_{37}$ via the CO); a phenylene (optionally substituted like for $B_{37}$); indanylene, or 1,2,3,4-tetrahydronaphthylene (saturated ring linked to $A_{37}$, the aromatic ring being linked to the carbamide portion); pyridinylene, pyrimidinylene, pyrazinylene, pyridazinylene or triazinylene (all optionally substituted on the carbon-containing backbone with an alkyl; it being possible for one or two —CH=N— groups of these rings to be replaced with a —CO—$NR_{37}^1$ group, and it being possible for a nitrogen atom to be attached to the $B_{37}$ radical instead of $R_{37}^1$ as long as the latter does not represent a bond or is not bonded to a heteroatom of the radical $C_{37}$); or $(C_4-C_5)$cycloalkylene, as defined for $B_{37}$;

a second radical selected from $R^a_{37}$ to $R^d_{37}$ represents a group of formula $F_{37}$—$E_{37}$—$D_{37}$—, in which $D_{37}$ is a $(C_1-C_5)$alkylene or a $(C_2-C_5)$alkenylene; a phenylene (optionally mono- or disubstituted with one or more identical or different substituents selected from F, Cl, Br, $(C_1-C_4)$alkyl, $CF_3$, OH, alkoxy, alkylthio, alkyl-SO—, alkyl-$SO_2$—, carboxyalkoxy, alkoxycarbonylalkoxy, aralkoxycarbonylalkoxy, $(R^1_{37})_2N$—, $(R^1_{37})_2NCO$—, $(R^1_{37})_2NSO_2$ or $NO_2$ or $R^1_{37}NH$— ($R^1_{37}NH$— being optionally substituted as indicated above); a pyridinylene, pyrimidinylene, pyrazinylene, pyridazinylene or triazinylene ring (all optionally substituted on the carbon-containing backbone with an alkyl; it being possible for one or two —CH=N— groups of these rings to be replaced with a —CO—$NR_{37}^1$ group, and it being possible for a nitrogen atom to be attached to the radical $E_{37}$ instead of $R^1_{37}$ as long as the latter does not represent a bond or is not bonded to a heteroatom of the radical $D_{37}$);

$(C_4-C_5)$cycloalkylene as defined above for $B_{37}$;

a $(C_4-C_5)$cycloalkylene as defined above for $B_{37}$, a $(C_6-C_7)$cycloalkylene as defined above for $B_{37}$, or a $(C_2-C_6)$alkylene group interrupted by the radical W in which W represents O, S, SO, $SO_2$, $R_{37}^1N$—, (alkylcarbonyl)N—, (aralkylcarbonyl)N—, (arylcarbonyl)N—, (heteroarylcarbonyl)N—, (alkylsulphonyl)N—, (arylsulphonyl)N—, aminocarbonyl- or carbonylamino;

$E_{37}$ is a bond, a $(C_1-C_5)$alkylene, or a $(C_2-C_5)$alkenylene (optionally substituted with one or two alkyl, or with an OH, alkoxy, $NH_2$, alkylamino, aralkylamino, dialkylamino, bis(aralkyl)amino, a carboxyalkyl, an alkoxycarbonylalkyl or an aralkoxycarbonylalkyl);

a phenylene (optionally substituted like for $B_{37}$); a pyridinylene, pyrimidinylene, pyrazinylene, pyridazylene or triazinylene ring (all optionally substituted on the carbon-containing backbone with an alkyl; it being possible for one or two —CH=N— groups to be replaced by a CO—$NR_{37}^1$ group and it being possible for a nitrogen atom to be bonded to the $D_{37}$ radical instead of the $R_{37}^1$ radical), a $(C_4–C_5)$ cycloalkylene group as defined for $D_{37}$; a $(C_6–C_7)$ cycloalkylene group as defined for $D_{37}$; an alkylenearylene(aryl linked to $D_{37}$); or an alkylene linked to $W_{37}$ of $D_{37}$;

$F_{37}$ is a carbonyl group substituted with OH or $(C_1–C_6)$ alkoxy (it being possible for a $(C_1–C_3)$alkoxy to be substituted on each of its positions with an aryl or a heteroaryl, or at the 2- or 3-position with a pyrrolidin-2-on-1-yl, morpholino, thiomorpholino or 1-oxidothiomorpholino); sulpho; phosphono; O-alkylphosphono or tetrazol-5-yl; it being understood that when $A_{37}$=CN or an amino or an aminoalkyl (the amino and aminoalkyl radicals being optionally benzoylated or benzyloxycarbonylated on the nitrogen atom), the shortest distance between the nitrogen atom of these groups and $F_{37}$ being at least 10 bonds;

a third radical selected from $R^a_{37}$ to $R^d_{37}$ is H, alkyl, perfluoroalkyl, aralkyl, aryl or heteroaryl, it being understood that this third radical, when it is linked to an unsaturated carbon atom of $Y_{37}$, may also be an alkoxy, an alkylthio or $(R^1_{37})_2N$;

a fourth radical selected from $R^a_{37}$ to $R^d_{37}$ is H, an alkyl, an aralkyl, an aryl or a heteroaryl; or $R^a_{37}$ or $R^b_{37}$ together with adjacent $R^c_{37}$ or $R^d_{37}$ represent a bond; it should be understood that unless otherwise defined (a) all the alkyl, alkylene, alkenylene or alkoxy have from 1 to 3 carbon atoms;

(b) aryl is phenyl (optionally substituted with a $CF_3$, COOH, $(R^1_{37})_2NCO$, alkoxycarbonyl, alkylcarbonyl, alkylthio, alkylsulphinyl, alkylsulphonyl, $NO_2$, $(R^1_{37})_2N$, alkylcarbonyl-$NR_{37}^3$—, aralkylcarbonyl-$NR_{37}^3$—, arylcarbonyl-$NR_{37}^3$—, heteroarylcarbonyl-$NR_{37}^3$—, alkylsulphonyl-$NR_{37}^3$, aralkylsulphonyl-$NR_{37}^3$, arylsulphonyl-$NR_{37}^3$, or $(R_{37}^3)_2N$-sulphonyl; or with 1 to 3 F, Cl, Br, OH or a $(C_1–C_4)$alkyl or alkoxy);

the heteroaryl is a 5-membered heteroaromatic ring with an oxygen atom, a sulphur atom or a nitrogen atom, a nitrogen atom and an oxygen atom, a sulphur atom or a nitrogen atom or two nitrogen atoms and an oxygen atom, a sulphur atom or a nitrogen atom, or a 6-membered heteroaromatic ring with one; two or three nitrogen atoms, and in which one or two —CH=N— groups may be replaced with a —CO—$NR_{37}^3$ group, it being understood that the said heteroaromatic rings may be substituted with one or two alkyl groups or with a fluorine, chlorine or bromine atom or with a hydroxyl or alkoxy group), and their tautomeric forms and their stereoisomers (or mixtures thereof) as well as their pharmaceutically acceptable salts as described in EP 503548.

XXVIII—SR 121787A or one of its analogs of formula:

(XXXVIII)

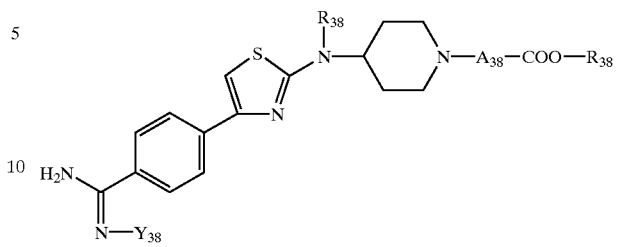

in which:

$R_{38}^1$ represents hydrogen, a $(C_1–C_5)$alkyl, a $(C_3–C_8)$ cycloalkyl, an aralkyl in which the alkyl portion is a $C_1–C_5$, an alkoxycarbonylalkyl group in which the alkoxy and alkyl portions are a $C_1–C_3$ or a carboxyalkyl group in which the alkyl portion is a $C_1–C_3$;

$A_{38}$ represents either a methylene group optionally mono- or disubstituted with a $(C_1–C_5)$alkyl group; with an alkoxycarbonyl group in which the alkoxy portion is a $C_1–C_5$; with an alkoxycarbonylalkyl group in which the alkoxy and alkyl portions are a $C_1–C_5$; with a carboxyalkyl group in which the alkyl portion is a $C_1–C_5$; with a phenyl or benzyl group unsubstituted or substituted on the aromatic ring with a $(C_1–C_5)$alkyl1, a $(C_1–C_5)$alkoxy, a hydroxyl, a halogen or a trifluoromethyl; with a pyridyl group; or an ethylene group;

$R_{38}$ represents hydrogen, or a $(C_1–C_5)$alkyl group; an aryl group or an aralkyl group in which the alkyl portion is a $C_1–C_5$ optionally substituted with a hydroxyl, a $(C_1–C_3)$alkoxy, a halogen, a trifluoromethyl or a $(C_1–C_5)$alkyl;

$Y_{38}$ represents hydrogen; a —$COOR_{38}^2$ group in which $R_{38}^2$ represents a $(C_1–C_5)$alkyl group, an aryl group or an aralkyl group in which the alkyl portion is a $C_1–C_5$ optionally substituted with a $(C_1–C_5)$alkyl; a —$COR_{38}^3$ group in which the $R_{38}^3$ represents a $(C_1–C_5)$alkyl; or one of their salts, as described in EP 719775.

XXXIX—FK 633 and its peptide analogues of formula:

(XXXIX)

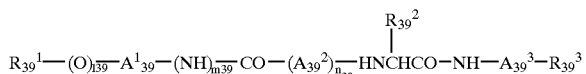

in which:

$R_{39}^1$ is a phenyl, naphthyl or anthryl group, in which each has 1 to 3 substituents selected from the group consisting of amidino and protected amidino groups, $R_{39}^2$ is a carboxy($C_1–C_6$ alkyl) or protected carboxy ($C_1–C_6$ alkyl) group, $R_{39}^3$ is a carboxyl or protected carboxyl group, $A_{39}^1$ is an alkylene group which may have 1 to 8 substituents selected from the group consisting of amino and protective amino groups, $A_{39}{}^2$ is a group of formula:

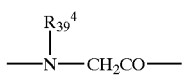

in which $R_{39}{}^4$ is a $(C_1-C_6)$alkyl group or a group of formula:

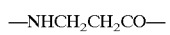

$A_{39}{}^3$ is a $(C_1-C_6)$alkylene group which may have 1 to 3 substituents selected from the group consisting of a $(C_1-C_6)$alkyl group; mono- (or di- or tri)phenyl $(C_1-C_6)$alkyl) group which may have 1 to 3 substituents selected from the group consisting of a hydroxyl, $(C_1-C_6)$alkoxy and protected hydroxyl group; hydroxy $(C_1-C_6$ alkyl) group; protected hydroxy$(C_1-C_6$ alkyl) group; $[C_5-C_6$ cycloalkyl]-$(C_1-C_6$ alkyl) group; and heterocyclyl$(C_1-C_6$ alkyl) group, in which the heterocyclic portion is a 3- to 8-membered unsaturated heteromonocyclic group containing 1 to 4 nitrogen atoms, a 3- to 8-membered unsaturated heteromonocyclic group containing 1 to 2 oxygen atoms and 1 to 3 nitrogen atoms, or a 3- to 8-membered unsaturated heteromonocyclic group containing 1 to 2 sulphur atoms and 1 to 3 nitrogen atoms;

$l_{39}$, m39 and $n_{39}$ are each identical or different and equal to the integer 0 or 1 provided that:

(i) when $l_{39}$ is an integer 0, $A_{39}{}^2$ is then not a group of formula

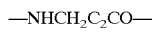

and (ii) when $l_{39}$ and $m_{39}$ are each the integer 0, $R_{39}{}^1$ is a phenyl group having an amidino or naphthyl substituent having an amidino substituent $R_{39}{}^2$ is a carboxymethyl or $(C_1-C_6$ alkoxy) carbonylmethyl group $R_{39}{}^3$ is a carboxyl group or a $(C_1-C_6$ alkoxy)carbonyl group, $R_{39}{}^4$ is a $(C_1-C_4)$alkyl group and $A_{39}{}^1$ is a $(C_1-C_6)$alkylene group, $A_{39}{}^3$ is then a $(C_1-C_6)$alkylene group which has a substituent selected from the group consisting of the groups: propyl, butyl, phenyl $(C_1-C_6$ alkyl) having a methoxy or ethoxy substituent; hydroxy$(C_1-C_6$ alkyl); and $[C_5-C_6$ cycloalkyl]-$(C_1-C_6$ alkyl);

(iii) when 139 is an integer 1, $m_{39}$ and $n_3$ are each the integer 0, $R_{39}{}^1$ is a 6-amidino-2-naphthyl group, $R_{39}{}^2$ is a carboxymethyl group $R_{39}{}^3$ is a carboxyl group $A_{39}{}^1$ is a methylene group, $A_{39}{}^3$ is then not a methylene group having a benzyl substituent, or one of its pharmaceutically acceptable salts, as described in EP 513675.

XXXX—Orbofiban or one of its lactam analogues of formula:

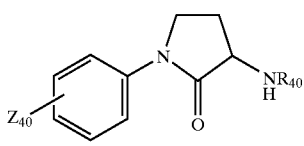

in which $R_{40}$ is a protecting group selected from the group consisting of t-butoxycarbonyl and carbobenzyloxy;

$Z_{40}$ is selected from the group consisting of —CN, —CONH$_2$ and CO$_2$ alkyl, as described in U.S. Pat. No. 5,484,946.

XXXXI—Alprostadil or its analogues of formula:

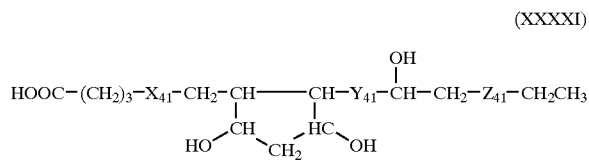

in which:

$X_{41}$ and $Z_{41}$ are —CH$_2$CH$_2$— and $Y_{41}$ is —CH$_2$—CH$_2$— or —CH=CH—, or in which:

$X_{41}$ and $Y_{41}$ are —CH=CH—, and $Z_{41}$ is —CH$_2$—CH$_2$—or —CH=CH— and its pharmaceutically acceptable salts, as described in GB 1,040,544.

XXXXII—Epoprostenol and its analogues of formula:

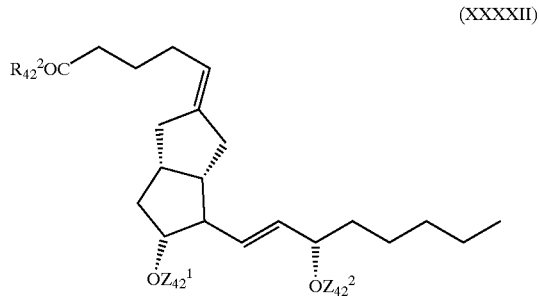

in which:

$R_{42}$ represents a hydrogen or a pharmacologically acceptable cation, and $Z_{42}{}^1$ and $Z_{42}{}^2$ are a hydrogen and/or a protecting group, as described in DE 2,720,999.

XXXXIII—Iloprost and its analogues of formula:

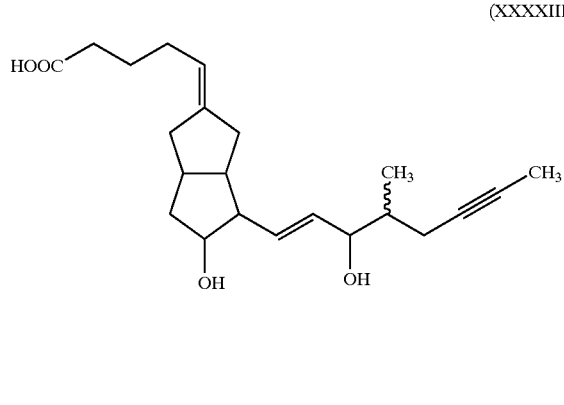

(XXXXIII)

or one of its derivatives described in Ger. pat. 2,845,770 and U.S. Pat. No. 4,692,464.

XXXXIV—Beraprost or one of its analogues of formula:

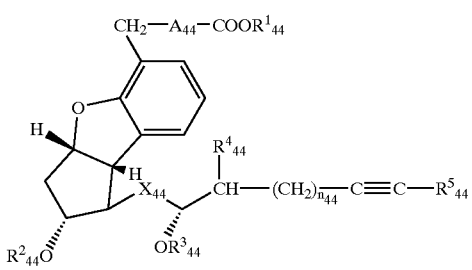

(XXXXIV)

in which:

$R^1_{44}$ is a pharmaceutically acceptable cation, a hydrogen atom or an n-alkyl group having from 1 to 12 carbon atoms;

$R^2_{44}$ is a hydrogen atom, an acyl group having 2 to 10 carbon atoms, or an aroyl group of 7 to 13 carbon atoms;

$R^3_{44}$ is a hydrogen atom, an acyl group of 2 to 10 carbon atoms or an aroyl group of 7 to 13 carbon atoms;

$R^4_{44}$ is a hydrogen atom, a methyl group or an ethyl group;

$R^5_{44}$ is an n-alkyl group of 1 to 5 carbon atoms;

$n_{44}$ is an integer from 0 to 4;

$A_{44}$ is a —CH$_2$—CH$_2$— or a trans —CH=CH—;

$X_{44}$ is a —CH$_2$—CH$_2$— or a trans —CH=CH—, as described in EP 84856.

XXXXV—Cicaprost or a 13,14,18,18,19,19-hexahydro-3-oxa-6a-carbaprostaglandin $I_2$ (5E) derivative corresponding to the formula:

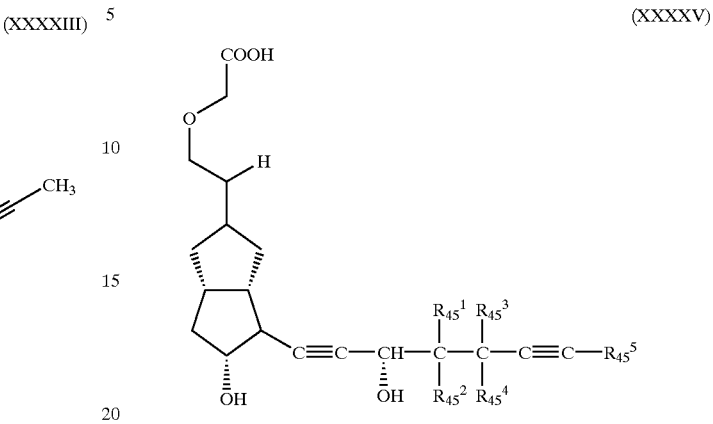

(XXXXV)

in which:

$R_{45}^1$, $R_{45}^2$, $R_{45}^3$ and $R_{45}^4$ each represent a hydrogen atom or an alkyl radical containing from 1 to 5 carbon atoms, and $R_{45}^5$ represents an alkyl radical containing 1 to 5 carbon atoms, as well as the salts which they form with physiologically acceptable bases, as described in EP 119949.

XXXXVI—Taprostene or a 2,3,4-trinor-1,5-inter-m-phenylene-6,9-epoxy-11,15-dihydroxy-5-prostenoic acid derivative of formula:

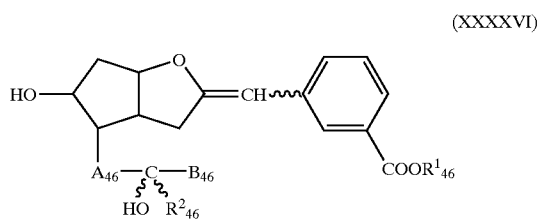

(XXXXVI)

in which:

1the carbon atom carrying $R^2_{46}$ may be racemic or of S configuration;

$R^1_{46}$ is hydrogen, a pharmaceutically acceptable cation or the residue of an alcohol which may be pharmaceutically used in an esterified form;

$R^{246}$ is hydrogen or CH$_2$;

$A_{46}$ is trans-vinylene or a 1,2-ethylene; and $B_{46}$ is the (C$_5$–C$_9$) residue of structure —C(R$^3_{46}$)(R$^{446}$)—(CH$_2$)$_3$—CH$_3$ in which R$^3_{46}$ and R$^{446}$ are each hydrogen, CH$^3$ or C$_2$H$_5$; or B$_{46}$ represents a cyclohexyl optionally substituted at the 4-position with CH$_3$ or a C$_2$H$_5$, as described in EP 45842.

XXXXVI—Ataprost or one of its derivatives of formula:

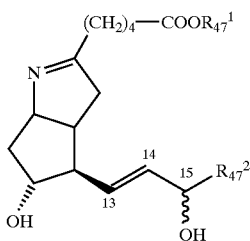

(XXXXVII)

in which:

$R_{47}^1$ represents a hydrogen atom or a lower alkyl group, $R_{47}^2$ represents a 2-methylhexyl group, a 3-propylcyclopentyl, 3-butylcyclopentyl, or a 4-propylcyclohexyl group; as defined in DE 3,316,356.

XXXXVIII—Ciprostene or a carbacycline analogue of formula:

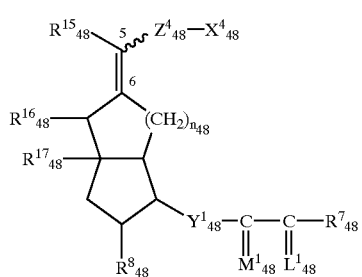

(XXXXVIII)

in which:

$n_{48}$ is one or two;

$L^1_{48}$ is $\alpha\text{-}R^3_{48}{:}\beta\text{-}R^4_{48}$, $\alpha\text{-}R^4_{48}{:}\beta\text{-}R^3_{48}$; or a mixture of $\alpha\text{-}R_{348}{:}\beta\text{-}R^4_{48}$ and of $\alpha\text{-}R^4_{48}{:}\beta\text{-}R^3_{48}$ in which:

$R^3_{48}$ and $R^4_{48}$ which are identical or different, are a hydrogen, a methyl or a fluorine, with the proviso that $R^3_{49}$ or $R^4_{48}$ is solely a fluorine if the other is a hydrogen or a fluorine;

$M^1_{48}$ is an $\alpha\text{-OH}{:}\beta\text{-}R^5_{48}$ or $\alpha\text{-}R^5_{48}{:}\beta\text{—OH}$ $R^5_{48}$ is a hydrogen or a methyl;

$R^7_{48}$ is:
(1) $-C_{m48}H_{2m48}-CH_3$, in which $m_{48}$ is an integer from 1 to 5,
(2) a phenoxy optionally substituted with one, two or three fluorine, chlorine or trifluoromethyl, a $(C_1-C_3)$ alkyl, or a $(C_1-C_3)$alkoxy, with the proviso that $R^7_{48}$ is a phenoxy or a substituted phenoxy only when $R^3_{48}$ and $R^4_{48}$, which are identical or different, are a hydrogen or a methyl,
(3) a phenyl, a benzyl, a phenylethyl, or a phenylpropyl optionally substituted on the aromatic ring with one, two or three chlorine, fluorine, or trifluoromethyl, a $(C_1-C_3)$alkyl, a $(C_1-C_3)$alkoxy, with the proviso that at most two substituents are different from an alkyl;
(4) cis-CH=CH—CH$_2$—CH$_3$,
(5) —(CH$_2$)$_2$—CH(OH)CH$_3$, or
(6) —(CH$_2$)$_3$—CH=C(CH$_3$)$_2$;

—C($L^1_{48}$)$R^7_{48}$ together represents:
(1) a $(C_4-C_7)$cycloalkyl optionally substituted with one to three $(C_1-C_5)$alkyl;
(2) a 2-(2-furyl)ethyl;
(3) a 2-(3-thienyl)ethoxy, or
(4) a 3-thienyloxymethyl;

$R^8_{48}$ is a hydroxyl, a hydroxymethyl or a hydrogen;

$R^{16}_{48}$ is hydrogen or a fluorine;

$R^{16}_{48}$ is a hydrogen or $R^{16}_{48}$ and $R^{17}_{48}$ together form a —CH$_2$—;

$R^{17}_{48}$ is defined as above or is
(1) a hydrogen,
(2) a $(C_1-C_4)$alkyl;
(1) $R^{20}_{48}$, $R^{21}_{48}$, $R^{22}_{48}$, $R^{23}_{48}$ and $R^{24}_{48}$ are all hydrogens with $R^{22}_{48}$ representing an $\alpha$-hydrogen or a $\beta$-hydrogen, or
(2) $R^{20}_{48}$ is a hydrogen, $R^{21}_{48}$ and $R^{22}_{48}$ together form a second bond with a valency between C-9 and C-6a and $R^{23}_{48}$ and $R^{24}_{48}$ together form a second bond with a valency between C-8 and C-9 or are both hydrogens, or
(3) $R^{22}_{48}$, $R_{2348}$ and $R^{24}_{48}$ are all hydrogen, with $R^{22}_{48}$ being either an $\alpha$-hydrogen or a $\beta$-hydrogen and
(a) $R^{20}_{48}$ and $R^{21}_{48}$ together are an oxo or
(b) $R^{20}_{48}$ is a hydrogen and $R^{21}_{48}$ is a hydroxyl, or an $\alpha$-hydroxyl or a $\beta$-hydroxyl;

$X^1_{48}$ is
(1) a —COOR$^1_{48}$ in which:

$R^1_{48}$ is
(a) a hydrogen
(b) a $(C_1-C_{12})$alkyl,
(c) a $(C_3-C_{10})$cycloalkyl,
(d) a $(C_7-C_{12})$aralkyl,
(e) a phenyl optionally substituted with one, two or three chlorine or a $(C_1-C_3)$alkyl,
(f) a phenyl substituted on the para position with an —NH—CO—R$^{25}_{48}$, a —CO—R$^{26}_{48}$, an —O—CO—R$^{24}_{48}$ or a —CH=N—NH—CO—NH$_2$ in which R$^{25}_{48}$ is a methyl, a phenyl, an acetamidophenyl, a benzamidophenyl or amino; R$^{26}_{48}$ is a methyl or phenyl, —NH$_2$ or methoxy; and $R_{24}^{48}$ is a phenyl or an acetamidophenyl, or
(g) a pharmaceutically/pharmacologically acceptable cation;
(2) a —CH$_2$OH,
(3) a —COL$^4_{48}$, in which:

$L^4_{48}$ is
(a) an amino of formula —NR$^{21}_{48}$R$^{22}_{48}$, in which $R^{21}_{48}$ and $R^{22}_{48}$ are a hydrogen, a $(C_1-C_{12})$alkyl; a $(C_3-C_{10})$cycloalkyl; a $(C_1-C_{12})$aralkyl; a phenyl optionally substituted with ones two or three chlorine, with $(C_1-C_3)$alkyl, with a hydroxyl, with a carboxyl, with a $(C_2-C_5)$alkoxycarbonyl, or with a nitro, a $(C_2-C_5)$carboxyalkyl; a $(C_2-C_5)$carbamoylalkyl; a $(C_2-C_5)$cyanoalkyl, a $(C_3-C_6)$acetylalkyl; a $(C_7-C_{11})$benzoalkyl optionally substituted with one, two or three chlorine, $(C_1-C_3)$alkyl, hydroxyl, $(C_1-C_3)$alkoxy, carboxyl, $(C_2-C_5)$alkoxycarbonyl or nitro; a pyridyl optionally substituted with one, two or three chlorine, $(C_1-C_3)$alkyl or $(C_1-C_3)$alkoxy; a $(C_3-C_9)$pyridylalkyl optionally substituted with one, two or three chlorine, $(C_1-C_3)$alkyl, hydroxyl, or $(C_1-C_3)$alkyl; a $(C_1-C_4)$ hydroxyalkyl; a $(C_1-C_4)$dihydroxyalkyl, a $(C_1-C_4)$ trihydroxyalkyl; with the additional limitation that only one radical from $R^{21}_{48}$ and $R^{22}_{48}$ is distinct from a hydrogen or an alkyl,
(b) a cyclic amine selected from the group consisting of pyrrolidino, piperidino, morpholino, piperazino, hexamethylenimino, pyrrolino, or 3,4-didehydropiperidinyl optionally substituted with one or two ($C_1$–$C_{12}$)alkyl, (c) a carbonylamino of formula —$NR^{23}_{48}COR^{21}_{48}$, in which $R^{23}_{48}$ is a hydrogen, or a ($C_1$–$C_4$)alkyl and $R^{21}_{48}$ is other than a hydrogen, and otherwise defined as above, (d) a sulphonylamino of formula —$NR^{23}_{48}SO_2R^{21}_{48}$, in which $R^{21}_{48}$ and $R^{23}_{48}$ are as defined for (c), (4) a —$CH_2NL^2_{48}L^3_{48}$ in which $L^{248}$ and $L^3_{48}$, which are identical or different, are hydrogen, or a ($C_1$–$C_4$) alkyl, or one of its pharmaceutically acceptable acid addition salts when $X^1_{48}$ is —$CH_2NL^2_{48}L^3_{48}$, $Y^1_{48}$ is trans-CH=CH—, cis-CH=CH—, —$CH_2CH_2$—, or —C≡C—;

$Z^1_{48}$ is (1) a —$CH_2$—$(CH_2)_{f48}$—$C(R^2_{48})_2$, in which:
$R^2_{48}$ is a hydrogen, or a fluorine and $f_{48}$ is 0, 1, 2 or 3

(2) a trans-$CH_2$—CH=CH—

(3) —(Ph) $(CH_2)_{g48}$— in which (Ph) is 1,2-, 1,3-, 1,4-phenylene, and $g_{48}$ is 0, 1, 2 or 3;

with the proviso that (1) $R^{15}_{48}$, $R^{16}_{48}$, $R^{17}_{48}$ are all hydrogens when —$Z^1_{48}$ is —(Ph) $(CH_2)_{g48}$— and (2) $Z^1_{48}$ is (Ph)—$(CH_2)_{g48}$— only if $R^{15}_{48}$ is a hydrogen, as defined in GB 2,070,596.

XXXXIX—Dipyramidole or its analogues selected from the group consisting of substituted basic dipyrimido-[5,4-d] pyrimides of formula:

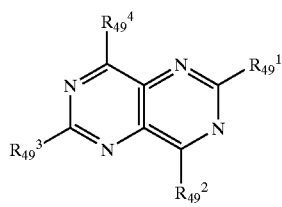

(XXXXIX)

in which from 2 to 4 of the substituents $R_{49}^1$, $R_{49}^2$, $R_{49}^3$, $R_{49}^4$ are basic entities selected from the group consisting of an amino, a lower alkylamino, a dialkylamino in which the alkyl entity has from 1 to 12 carbon atoms, a monohydroxy (lower alkyl)amino, a di(lower hydroxyalkyl)alkylamino in which the alkyl entity has from 1 to 12 carbon atoms, a (lower alkoxy-lower alkyl)amino, a (lower alkenyl)amino, a cyclohexylamino, a phenylamino, a halophenylamino, a nitrophenylamino, a (lower alkoxyphenyl)amino, a [(lower dialkylamino)phenyl]amino, a benzylamino, a semicarbazidyl, a hydrazinyl, a guanidyl, an ethylenimino, a piperidyl, a lower alkylpiperidyl, a lower alkoxypiperidyl, a hydroxypiperidyl, a pyrrolidyl, a lower alkylpyrrolidyl, a lower alkoxypyrrolidyl, a hydroxypyrrolidyl, a morpholyl, a lower alkylmorpholyl, a lower alkoxymorpholyl, a hydroxymorpholyl, a tetrahydropyridyl, a lower alkyltetrahydropyridyl, a lower alkoxytetrahydropyridyl, a hydroxytetrahydropyridyl, a hexamethylenimnino, a lower alkylhexamethylenimino, a lower alkoxyhexamethylenimino, a hydroxyhexamethylenimino, a tetrahydroquinolyl, a lower alkyltetrahydroquinolyl, a lower alkoxytetrahydroquinolyl, a hydroxytetrahydroquinolyl, a piperazyl, a lower alkylpiperazyl, a lower alkoxypiperazyl, a hydroxypiperazyl, and a lower N'-alkylpiperazyl, and the substituents remaining $R_{49}^1$ to $R_{49}^4$ are selected from the group consisting of hydrogen, halogen, hydroxyl, mercapto, lower alkyl, phenyl, lower alkoxy, lower dialkylamino (lower alkoxy), and a lower alkylthio, a phenylthio, a benzylthio, a lower alkoxyalkoxy, their nontoxic alkali metal salts and their nontoxic addition salts with an acid, as described in U.S. Pat. No. 3,031,450.

L—Cilostazol or one of its analogues of formula:

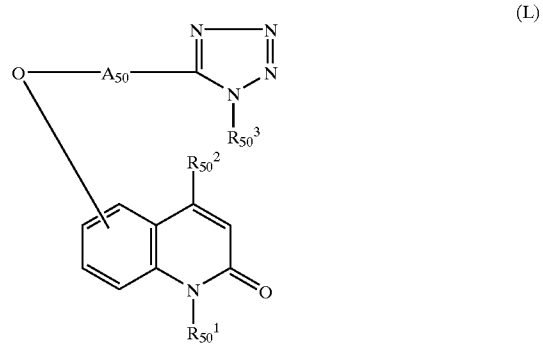

(L)

in which:

$R_{50}^1$ represents a hydrogen atom, a lower alkyl group, a lower alkenyl group, a lower alkanoyl group, a benzoyl group or a phenylalkyl group;

$R_{50}^2$ represents a hydrogen atom, a lower alkyl group or a group of formula:

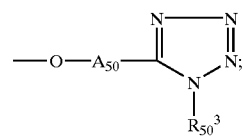

$R_{50}^3$ represents a lower alkyl group, a cycloalkyl group, a cycloalkylalkyl group, a phenyl group or a phenylalkyl group;

$A_{50}$ represents a lower alkylene group;

the carbon-carbon bond between the 3- and 4-positions of the carbostyrile backbone is a single bond or a double bond;

and the position of the group corresponding to the formula

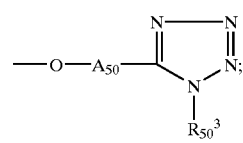

on the carbostyrile backbone is the 4-, 5-, 6-, 7- or 8-position with the proviso that a single group of formula above can be attached to the entire carbostyrile backbone, thus, when $R_{50}^2$ at the 4-position represents

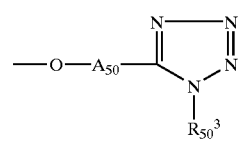

5-, 6-, 7- or 8-positions do not have such a group, it being possible for the phenyl group of the abovementioned benzoyl, phenylalkyl or phenyl groups to have one or more substituents, as described in BE 878 548.

The preferred antiplatelet aggregating agents are aspirin, ticlopidine, clopidogrel or antagonists of glycoprotein IIb/

IIIa. It will be noted, however, that the use of aspirin is not recommended in patients having undergone a revascularization procedure such as a percutaneous angioplasty. The preferred glycoprotein IIb/IIIa antagonists are:

ethyl N-(1-ethoxycarbonylmethylpiperidin-4-yl)-N-{4-[4-{(N-ethoxycarbonylimino)(amino)methyl}phenyl]thiazol-2-yl}-3-aminopropionate, designated SR 121787A, and its pharmaceutically acceptable salts, and N-(1-carboxymethylpiperidin-4-yl)-N-{4-[4-{(amino)(imino)methyl}phenyl]thiazol-2-yl}-3-aminopropionic acid, and its pharmaceutically acceptable salts, such as the trihydrochloride, designated SR 121566.

The formulae of SR 121787 and of SR\121566 are recalled below:

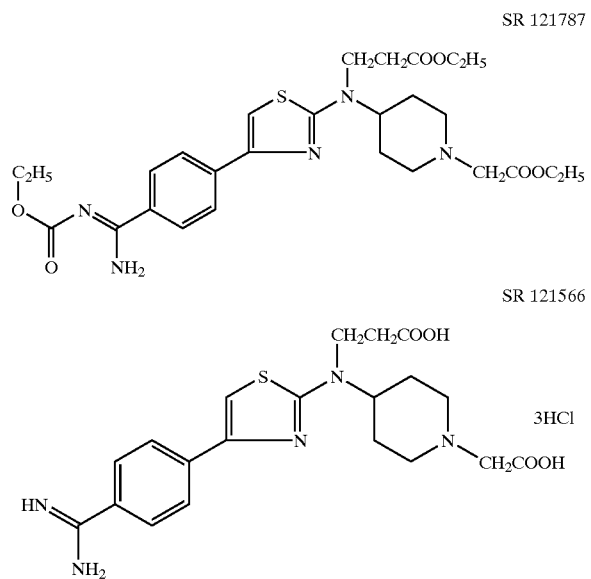

The selective inhibitor of factor Xa, alone or in combination with an anti-platelet aggregation agent, is particularly useful for the treatment or prophylaxis of pathological conditions such as disorders of the cardiovascular or cerebrovascular system such as thromboembolic disorders associated with atherosclerosis or with diabetes such as unstable angina, cerebral attack, restenosis following angioplasty, endarterectomy or fitting of metallic endovascular prostheses, or such as thromboembolic disorders associated with rethrombosis following thrombolysis, with infarction, with dementia of ischaemic origin, with peripheral arterial diseases, with haemodialysis, with atrial fibrillations, or during the use of vascular prostheses, of aortocoronary bypasses or for stable or unstable angina, or for patients treated by a revascularization procedure at the risk of thrombosis including percutaneous angioplasties, endovascular prostheses, vascular prostheses, aortocoronary bypasses.

As examples of pharmaceutically acceptable organic salts, there may be mentioned oxalate, maleate, fumarate, methanesulphonate, benzoate, ascorbate, pamoate, succinate, hexamate, bismethylenesalicylate, ethanedisulphonate, acetate, propionate, tartrate, salicylate, citrate, gluconate, lactate, malate, cinnamate, mandelate, citraconate, aspargate, palmitate, stearate, itaconate, glycolate, p-aminobenzoate, glutamate, benzenesulphonate and theophylline acetate as well as the salts formed from an amino acid such as the lysine or histidine salt.

As examples of pharmaceutically acceptable inorganic salts, there may be mentioned hydrochloride, hydrobromide, sulphate, sulphamate, phosphate and nitrate.

The neutralization of activated factor X (Xa) (by antithrombin III) can be catalysed by the pentasaccharide (PS) such as low-molecular-weight heparin. Unlike the low-molecular weight heparin, the pentasaccharide is completely devoid of activated thrombin. In addition, the pentasaccharide hardly modifies the haemostasis tests and in particular the activated partial thromboplastin time (APTT) test on human plasma and unlike heparin, it does not potentiate ADP or platelet aggregation induced by collagen.

However, the antithrombotic effects of the pentasaccharide have been demonstrated after intravenous (i.v.) and subcutaneous (s.c.) administration in different animal models with different types of induced thromboses (the venous stasis model in rats, the arteriovenous shunt model in rats, the Wessler model in rabbits) (Hobellen P M J et al, Tromb. & Haemost., 1996, 63(2), 265–270 and Amar J. et al, Br. J. Haematol., 1990, 76, 94–100). As regards the risk of bleeding, the loss of blood at high PS dose tested in rats (21.7 mg/kg) is identical to that observed with 200 units anti-Xa/kg of heparin, thus indicating that PS only slightly increases blood loss compared with standard heparin or LMWHs.

To illustrate the invention and by way of example, there will be given below the results obtained during the study of the potentiation of the antithrombotic effect in rabbits by co-administration of a selective inhibitor of factor Xa and of an anti-platelet aggregation agent. As selective inhibitor of factor Xa, SR 90107/ORG 31540 (or PS) was selected and the anti-platelet aggregation agent was selected from the antagonists of glycoprotein IIb/IIIa, namely SR 121787A.

The aim of this test was therefore to determine the arterial antithrombotic effects of the co-administration of an anti-Xa, the pentasaccharide SR 90107/ORG 31540 and of an antagonist of the GPIIb/IIIa receptors, SR 121787A.

New Zealand male rabbits weighing 2.7 to 3 kg, obtained from the Lago breeding unit (France) were used. They were housed under standard conditions.

The formation of the thrombus was induced by external electrical stimulation of the left common carotid according to the Hladovec I. et al. method (Experimental arterial thrombosis in rats with continuous registration, Throm. Diathes. Haemor. 1971; 26: 407–410). The rabbits were anaesthetized with pentobarbital at the dose of 30 mg/kg iv. A segment of the left carotid artery was exposed and insulated by a piece of insulating film. Electrodes were inserted under the artery. A partial stricture inducing a 20% reduction in flow rate was made in the artery. The latter was then stimulated with the aid of a 2.5 mA current delivered by a constant current stimulator for 3 minutes. The thrombotic occlusion was evaluated by continuous measurement of the flow rate of blood in the carotid by means of an NARCO electromagnetic flow meter. This measurement was made over an observation period of 45 minutes.

For the treatment, solutions of SR 90107/ORG 31540 and of SR 121787A were prepared immediately before use in a saline solution. The solutions of SR 90107/ORG 31540 were injected by the IV route 5 minutes before induction of thrombosis in a volume of 1 ml/kg. SR 121787A was dadministered by the oral route 2 hours earlier.

The results were calculated and expressed as % reduction in blood flow rate at various times relative to time 0. They are grouped together in FIG. 1.

In the control animals, the flow rate was gradually reduced from 20.9±2.1 to 3.8±2.5 ml/min (n=8: mean for 8 animals) over 15 minutes and 1.5±1.4 ml/min over 20 min. It then stayed at this level for up to 45 minutes. SR-90107/ORG 31540, at the dose of 300 nmol/kg, had no influence on this reduction in flow rate. 600 nmol/kg of SR 90107/ORG 31540 reduced it slightly but not significantly.

SR 121787A administered 2 hours before as sole active ingredient at the oral dose of 10 mg/kg, did not significantly modify the course of the carotid output whereas 20 mg/kg almost completely inhibited the drop in the latter.

The co-administration of the pentasaccharide SR 90107/ORG 31540 and of the antagonist of the GPIIb/IIIa receptor SR 121787A, at doses which are separately inactive (300 nmol/kg iv and 10 mg/kg po, respectively) completely protected against reduction in flow rate and therefore against the arterial thrombosis thus induced.

No toxicological effect of SR 90107/ORG 31540 was observed on any animal species whatsoever, regardless of the concentration tested in the appropriate toxicity studies and by repeated assays (over a period of 4 weeks with up to 10 mg/kg subcutaneously). SR 90107/ORG 31540 is not mutagenic in the AMES test, or in the DNA repair test.

Thus, the use of a direct selective inhibitor of factor Xa, such as DX-9065a or of an indirect selective inhibitor of factor Xa, such as an oligosaccharide, alone or in combination with an anti-platelet aggregation agent, is particularly beneficial for pathological conditions such as disorders of the cardiovascular and cerebrovascular system such as thromboembolic disorders associated with atherosclerosis or with diabetes such as unstable angina, cerebral attack, restenosis following angioplasty, endarterectomy or fitting of metallic endovascular prostheses or such as thromboembolic disorders associated with rethrombosis following thrombolysis, with infarction, with dementia of ischaemic origin, with peripheral arterial diseases, with haemodialysis, with atrial fibrillations or during the use of vascular prostheses or of aortocoronary bypasses, or for stable or unstable angina, or for patients treated by a revascularization procedure at risk of thrombosis including percutaneous angioplasties, endovascular prostheses, vascular prostheses, aortocoronary bypasses.

In addition, the use of a direct selective inhibitor of factor Xa, such as DX-9065a or of an indirect selective inhibitor of factor Xa, such as an oligosaccharide, alone or in combination with the anti-platelet aggregation agents, does not increase the haemorrhagic risk.

The combination of a direct selective inhibitor of factor Xa, such as DX-9065a or of an indirect selective inhibitor of factor Xa, such as an oligosaccharide and of the anti-platelet aggregation agent may be formulated in pharmaceutical compositions which can be used by the oral or parenteral route, in particular by the subcutaneous route, in the form of a mixture with conventional pharmaceutical excipients.

Thus, according to another of its features, the invention relates to the pharmaceutical compositions comprising one or more direct or indirect selective inhibitors of factor Xa acting via antithrombin III in combination with one or more compounds with anti-platelet aggregation activity, and optionally one or more pharmaceutically acceptable vehicles.

The preferred pharmaceutical compositions of the invention comprise an antagonist of glycoprotein IIb/IIIa as anti-platelet aggregation agent and methyl O-(2-deoxy-2-sulphoamino-6-O-sulfo-α-D-glucopyranosyl)-(1→4)-O-, (β-D-glucopyranosyluronic acid-(1→4)-O-(2-deoxy-2-sulphoamino-3,6-di-O-sulpho-α-D-glucopyranosyl-(1→4)-O-(2-O-sulpho-α-L-idopyranosyluronic acid)-(1→4)-2-deoxy-2-sulphoamino-6-O-sulpho-α-D-glucopyranoside whose anion has the structure (B)

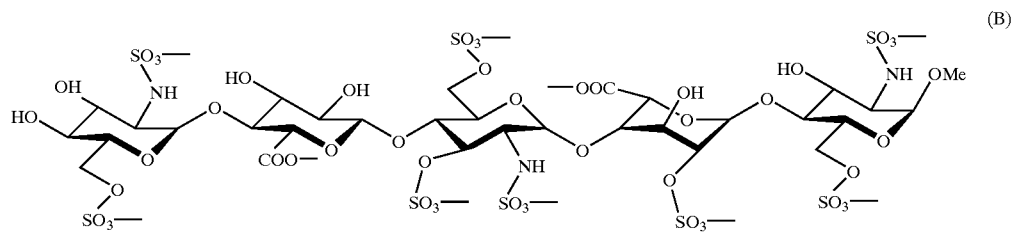

or one of its pharmaceutically acceptable salts, as indirect selective inhibitor of factor Xa.

Another preferred group of pharmaceutical compositions consists of the compositions comprising methyl O-(2-deoxy-2-sulphoamino-6-O-sulfo-α-D-glucopyranosyl-(1→4)-O-(β-D-glucopyranosyluronic acid-(1→4)-O-(2-deoxy-2-sulphoamino-3,6-di-O-sulpho-α-D-glucopyranosyl-(1→4)-O-(2-O-sulpho-α-L-idopyranosyluronic acid)-(1→4)-2-deoxy-2-sulphoamino-6-O-sulpho-α-D-glucopyranoside whose anion has the structure (B)

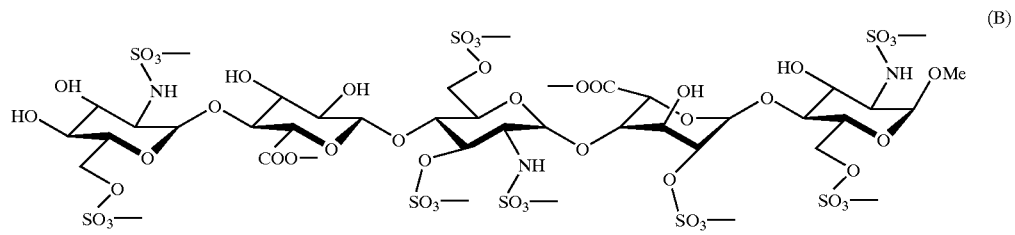

or one of its pharmaceutically acceptable salts, as indirect selective inhibitor of factor Xa, and aspirin, as anti-platelet aggregation agent.

The pharmaceutical compositions which are the subject of the present invention are preferably provided in the form of dosage units containing a predetermined quantity of the active ingredients, as specified below. The unit forms for administration by the oral route comprise tablets, gelatin capsules, powders, granules, microgranules.

The anti-platelet aggregation agent may be formulated according to methods well known to persons skilled in the art. The same applies to the selective inhibitor of factor Xa.

In the formulation of the combinations of active ingredients for the preparation of the pharmaceutical compositions according to the present invention, the nature of the active ingredients entering into the combination will be taken into account.

Thus, when the selective inhibitor of factor Xa is an oligosaccharide, the latter is preferably used in the form of an addition salt in the composition, for example in the form of a sodium salt.

Normally, the oligosaccharides in the form of their addition salts with pharmaceutically acceptable acids are not chemically incompatible with the nonsalified anti-platelet aggregation agents. However, some of the latter are also used in the form of acid addition salts. In any case, it is preferable to keep the active ingredients separate according to techniques well known in the literature.

The pharmaceutical compositions of the present invention are particularly suitable in the treatment or prophylaxis of pathological conditions such as disorders of the cardiovascular and cerebrovascular system such as thromboembolic disorders associated with atherosclerosis or with diabetes such as unstable angina, cerebral attack, restenosis following angioplasty, endarterectomy or fitting of metallic endovascular prostheses, or such as thromboembolic disorders associated with rethrombosis following thrombolysis, with infarction, with dementia of ischaemic origin, with peripheral arterial diseases, with haemodialysis, with atrial fibrillations, or during the use of vascular prostheses, of aortocoronary bypasses or for stable or unstable angina, or for patients treated by a revascularization procedure at risk of thrombosis including percutaneous angioplasties, endovascular prostheses, vascular prostheses and aortocoronary bypasses.

The combinations according to the invention may be formulated in pharmaceutical compositions for administration to mammals, including humans, for the treatment of the abovementioned diseases.

The combinations according to the invention may be used at daily doses of the selective inhibitor of factor Xa or of the anti-platelet aggregation agent of 0.1 to 100 mg per kilo of body weight of the mammal to be treated.

In human beings, the dose may vary for each of the components from 1 to 500 mg per day, according to the age of the subject to be treated and the type of treatment: prophylactic or curative. Preferably, the pentasaccharide is administered at doses of between 0.30 mg and 30 mg per patient and per day.

In the pharmaceutical compositions of the present invention, the active ingredients are generally formulated in dosage units containing from 0.1 to 50 mg of the said active ingredient per dosage unit.

The compositions of the invention are prepared so as to be able to be administered by the digestive or parenteral route and are provided in various forms, such as for example of injectable or oral solutions, sugar-coated tablets, plain tablets or gelatin capsules. The injectable solutions are the preferred pharmaceutical forms.

In the pharmaceutical compositions of the present invention for oral, sublingual, subcutaneous, intramuscular, intravenous, transdermal, transmucosa, local or rectal administration, the active ingredient may be administered in unit forms for administration, in the form of a mixture with conventional pharmaceutical carriers, to animals and to human beings. The appropriate unit forms for administration comprise the forms to be administered by the oral route, such as tablets, gelatin capsules, powders, granules and oral solutions or suspensions, the forms for sublingual or buccal administration, the forms for subcutaneous, intramuscular, intravenous, intranasal or intraocular administration and the forms for rectal administration.

When a solid composition in the form of tablets is prepared, the principal active ingredient is mixed with a pharmaceutical vehicle such as gelatin, starch, lactose, magnesium stearate, talc, gum arabic and the like. The tablets may be coated with sucrose or other appropriate materials or they may be treated such that they have a prolonged or delayed activity and that they continuously release a predetermined quantity of active ingredient.

A preparation of gelatin capsules is obtained by mixing the active ingredient with a diluent and by pouring the mixture obtained into soft or hard gelatin capsules.

The water-dispersible powders or granules may contain the active ingredient in the form of a mixture with dispersing agents or wetting agents, or suspending agents, such as polyvinylpyrrolidone, as well as with sweeteners or with flavour correctors.

For a rectal administration, suppositories are used which are prepared with binding agents which melt at the rectal temperature, for example cocoa butter or polyethylene glycols.

For a parenteral, intranasal or intraocular administration, aqueous suspensions, isotonic saline solutions or sterile and injectable solutions are used which contain pharmacologically compatible dispersing agents and/or wetting agents, for example propylene glycol or butylene glycol.

For transmucosa administration, the active ingredients may be formulated in the presence of a promoter. such as a bile salt, a hydrophilic polymer such as for example hydropropylcellulose, hydroxypropylmethylcellulose, hydroxyethylcellulose, ethyl cellulose, carboxymethylcellulose, dextran, polyvinylpyrrolidone, pectins, starches, gelatin, casein, acrylic acids, acrylic esters and their copolymers, vinyl polymers or copolymers, vinyl alcohols, alkoxy polymers, polyethylene oxide polymers, polyethers or their mixture.

The active ingredients may also be formulated in the form of microcapsules, optionally with one or more carriers or additives.

The active ingredients may also be provided in the form of a complex with a cyclodextrin, for example α-, β- or γ-cyclodextrin, 2-hydroxypropyl-β-cyclodextrin or methyl-β-cyclodextrin.

One of the active ingredients, for example the oligosaccharide, inhibitor of factor Xa, may also be released by a balloon containing it and by an endovascular expander introduced into the blood vessels. The pharmacological efficacy of the active ingredient is thus not affected.

Preferably, the selective inhibitor of factor Xa is administered by the intravenous or subcutaneous route.

In the therapeutic combinations according to the present invention, the pharmaceutical forms preferably contain 8 to 30 mg of selective inhibitor of factor Xa and 10 to 200 mg of anti-platelet aggregation compound.

The combination of 15 to 25 mg of selective inhibitor of factor Xa and of 10 to 30 mg of anti-platelet aggregation agent is particularly advantageous. Better still, the pharmaceutical forms of the present invention comprise 20 mg of a pentasaccharide, selective inhibitor of factor Xa, and 20 mg of an anti-platelet aggregation agent.

What is claimed is:

1. A method for the treatment or prophylaxis of thromboembolic arterial diseases which comprises administering to a patient in need of such treatment a synergistic effective amounts of methyl O-(2-deoxy-2-sulphoamino-6-O-sulfo-α-D-glucopyranosyl)-(1→4)-O-(β-D-glucopyranosyluronic acid)-(1→4)-O-(2-deoxy-2-sulphoamino-3,6-di-O-sulpho-α-D-glucopyranosyl-(1→4)-O-(2-O-sulpho-α-L-idopyranosyluronic acid)-(1→4)-2-deoxy-2-sulphoamino-6-O-sulpho-α-D-glucopyranoside having, in anionic form, the formula

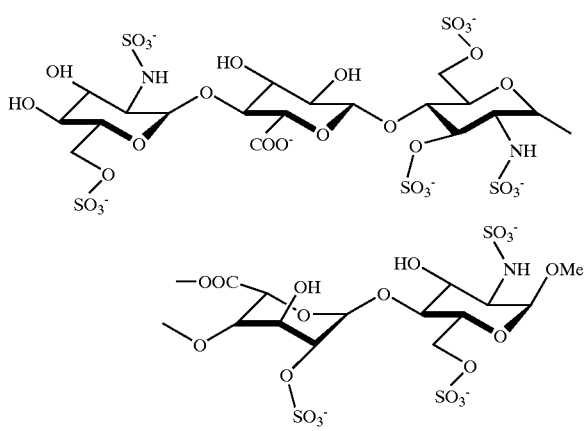

or a pharmaceutically acceptable salt thereof in combination with ethyl N-(1-ethoxycarbonylmethylpiperidin-4-yl)-N-(4-[4-((N-ethoxycarbonylimino)(amino)methyl)phenyl]-thiazol-2-yl)-3-aminopropionate having the formula

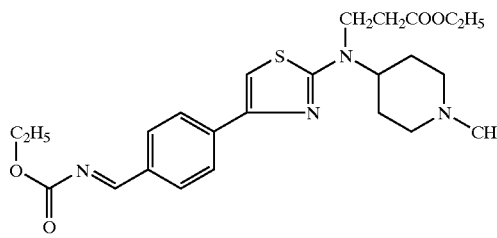

or a pharmaceutically acceptable, salt thereof.

2. A pharmaceutical composition comprising a synergistic effective amounts of methyl O-(2-deoxy-2-sulphoamino-6-O-sulfo-α-D-glucopyranosyl)-(1→4)-O-(β-D-glucopyranosyluronic acid)-(1→4)-O-(2-deoxy-2-sulphoamino-3,6-di-O-sulpho-α-D-glucopyranosyl-(1→4)-O-(2-O-sulpho-α-L-idopyranosyluronic acid)-(1→4)-2-deoxy-2-sulphoamino-6-O-sulpho-α-D-glucopyranoside having, in anionic form, the formula

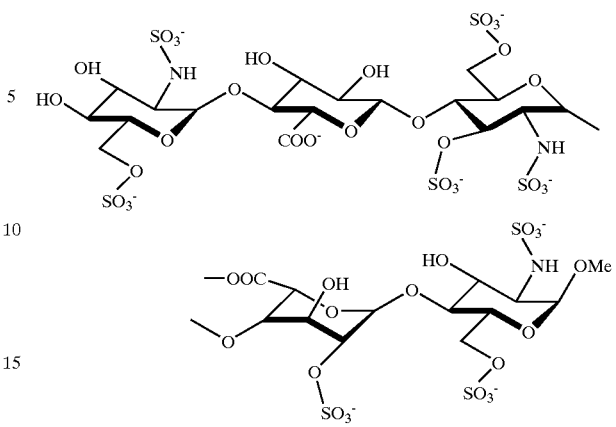

or a pharmaceutically acceptable salt thereof in combination with ethyl N-(1-ethoxycarbonylmethylpiperidin-4-yl)-N-(4-[4-((N-ethoxycarbonylimino)(amino)methyl)phenyl]-thiazol-2-yl)-3-aminopropionate having the formula

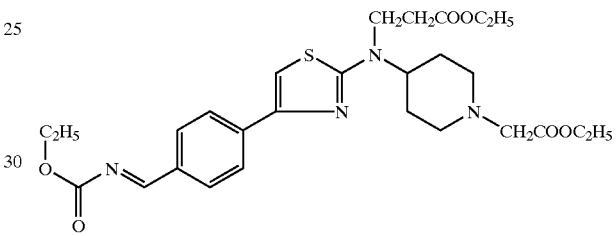

or a pharmaceutically acceptable salt thereof.

3. A method according to claim 1 wherein said thromboembolic arterial diseases are selected from disorders of the cardiovascular or cerebrovascular system.

4. A method according to claim 3 wherein said disorders of the cardiovascular or cerebrovascular system are thromboembolic disorders associated with atherosclerosis, with diabetes, with rethrombosis following thrombolysis, with infarction, with dementia of ischaemic origin, with peripheral arterial diseases, with haemodialysis, with atrial fibrillations, or during the use of vascular prostheses, of aortocoronary bypasses or for stable or unstable angina, or for patients treated by a revascularization procedure at the risk of thrombosis.

5. A method according to claim 4 wherein said thromboembolic disorders associated with atherosclerosis with diabete are selected from unstable angina, cerebral attack, restenosis following angioplasty, endarterectomy or the fitting of metallic endovascular prosthesis.

6. A method according to claim 4 wherein said revascularization procedure at the risk of thrombosis is selected from percutaneous angioplasties, endovascular prostheses, vascular prostheses or aortocoronary bypasses.

* * * * *